US006428781B1

(12) United States Patent
Sakano et al.

(10) Patent No.: US 6,428,781 B1
(45) Date of Patent: Aug. 6, 2002

(54) COMPOSITION OF AN ENDOGENOUS INSULIN-LIKE GROWTH FACTOR-II DERIVATIVE

(75) Inventors: Katsuichi Sakano; Nobuyuki Higashihashi; Ryuji Hashimoto, all of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/331,851

(22) PCT Filed: Dec. 26, 1997

(86) PCT No.: PCT/JP97/04881

§ 371 (c)(1),
(2), (4) Date: Jun. 28, 1999

(87) PCT Pub. No.: WO98/29451

PCT Pub. Date: Jul. 9, 1998

(30) Foreign Application Priority Data

Dec. 27, 1996 (JP) .............................................. 8-349968

(51) Int. Cl.[7] ........................ A61K 45/00; A61K 38/00; A61K 38/18; C07K 2/00; C07K 14/00

(52) U.S. Cl. ........................ 424/85.1; 424/198.1; 514/2; 514/12; 530/300; 530/303; 530/350; 530/399

(58) Field of Search ................................ 435/69.1, 69.4; 514/2, 3, 12; 530/300, 303, 350, 399; 424/85.1, 198.1

(56) References Cited

FOREIGN PATENT DOCUMENTS

| JP | 53-14605 B2 | 5/1978 |
| JP | 1-104077 A | 4/1989 |
| JP | 5-52806 B2 | 8/1993 |
| JP | 6-508743 A | 10/1994 |
| WO | WO97/39032 A1 | 10/1997 |

OTHER PUBLICATIONS

Bach et al. Binding of mutants of human insulin–like growth factor II to insulin–like growth factor binding proteins 1–6. J Biol Chem 268(12): 9246–9254, 1993.*
Beukers et al. Leu27 insulin–like growth factor II is highly selective for the type II IGF receptor in binding, cross–linking and thymidine incorporation experiments. Endocrinol 128(2): 1201–1203, 1991.*
Bach et al. Towards identification of a binding site on insulin–like growth factor II for IGF–binding proteins. Adv Exp Med Biol 343: 55–61, 1993.*
Hashimoto et al. Binding sites and binding properties of binary and ternary complexes of insulin–like growth factor–II (IGF–II), IGF–binding protein–3, and acid labile subunit. J Biol Chem 272(44): 27936–27942, 1997.*

Sakano et al. The design, expression, and characterization of human insulin–like growth factor–II (IGF–II) mutants specific doe wither the IGF–II/cation–independent mannose 6–phosphate receptor or IGF–I receptor. J Biol Chem 266(31): 20626–20635, 1991.*
Turkaij et al. Effect of increasing doses of recombinant human insulin–like growth factor–I on glucose, lipid, and leucine metabolism in man. J Clin Endocrinol Metab 75: 1186–1191, 1992.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10):425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding problem and Tertiary Structure Prediction, pp. 492–495, 1994.*
Booth et al.; Intrinsic Bioactivity of Insulin–Like Growth Factor–Binding Proteins from Vascular Endothelial Cells; Endocrinology; vol. 127 No. 6; pp. 2630–2638.
Yang et al.; Heparin Inhibition of Insulin–Like Growth Factor–Binding Protein–3 Binding to Human Fibroblasts and Rat Glioma Cells: Role of Heparan Sulfate Proteoglycans; Endocrinology; vol. 137 No. 10; pp. 4363–4371.

* cited by examiner

Primary Examiner—Elizabeth Kemmerer
Assistant Examiner—Bridget E. Bunner
(74) Attorney, Agent, or Firm—Sughrue Mion, PLLC

(57) ABSTRACT

The effects of endogenous insulin-like growth factor can be appreciated by administering compounds capable of increasing free IGF in living bodies. Compounds are described which can elevate the concentration of unbound IGF by converting endogenous IGF (insulin-like growth factor) into free, biologically active IGF or elevating the concentration of the complex of IGF and IGFBP (insulin-like growth factor binding protein) in living bodies. Medicaments can be prepared containing these compounds or these compounds may be used in methods for the prevention and or treatment of IGF-responsive diseases such as diabetes, amyotrophic lateral sclerosis, or osteoporosis.

7 Claims, 12 Drawing Sheets

MCS1:HindIII-PstI
MCS2:XbaI-BamHI-SmaI-KpnI-SacI-EcoRI

MCS1:HindIII-SphI-PstI
MCS2:SphI-XbaI-BamHI-SmaI-KpnI-SacI-EcoRI

MCS1:HindIII-PstI
MCS2:XbaI-BamHI-SmaI-KpnI-SacI-EcoRI

MCS2:XbaI-BamHI-SmaI-KpnI-SacI-EcoRI

SEQUENCE LISTING

```
<160> NUMBER OF SEQ ID NOS: 6

<210> SEQ ID NO 1
<211> LENGTH: 20
<212> TYPE: DNA
<213> ORGANISM: Rattus norvegicus
<220> FEATURE:
<221> NAME/KEY: STS
<222> LOCATION: (1)..(20)
<223> OTHER INFORMATION: One of PCR primers for cloning of the 5' end of
      IGFBP-3 gene from rat pancreas cDNA library
      The Sequence is described at page 38, line 19
      of the specification.
<300> PUBLICATION INFORMATION:
<301> AUTHORS: Shimasaki, S.
<303> JOURNAL: Biochem. Biophys. Res. Commun.
<304> VOLUME: 165
<306> PAGES: 907-
<307> DATE: 1989

<400> SEQUENCE: 1
cgccatgcat cccgcgcgcc                                                 20

<210> SEQ ID NO 2
```

```
<211> LENGTH: 20
<212> TYPE: DNA
<213> ORGANISM: Rattus norvegicus
<220> FEATURE:
<221> NAME/KEY: STS
<222> LOCATION: (1)..(20)
<223> OTHER INFORMATION: Another PCR primer for cloning of the 5' end of
      IGFBP-3 gene from rat pancreas cDNA library
      The Sequence is described at page 38, line 20
      of the specification.
<300> PUBLICATION INFORMATION:
<301> AUTHORS: Shimasaki, S.
<303> JOURNAL: Biochem. Biophys. Res. Commun.
<304> VOLUME: 165
<306> PAGES: 907-
<307> DATE: 1989

<400> SEQUENCE: 2
acgccgcacg cgtcgccttc                                           20

<210> SEQ ID NO 3
<211> LENGTH: 30
<212> TYPE: DNA
<213> ORGANISM: Rattus norvegicus
<220> FEATURE:
<221> NAME/KEY: STS
<222> LOCATION: (1)..(30)
<223> OTHER INFORMATION: One of PCR primers for cloning of the 3' end of
      IGFBP-3 gene from rat pancreas cDNA library
      The Sequence is described at page 38, line 22
      of the specification.
<300> PUBLICATION INFORMATION:
<301> AUTHORS: Shimasaki, S.
<303> JOURNAL: Biochem. Biophys. Res. Commun.
<304> VOLUME: 165
<306> PAGES: 907-
<307> DATE: 1989

<400> SEQUENCE: 3
gcgcgggccc cgtggtgcgc tgcgaaccgt                                30

<210> SEQ ID NO 4
<211> LENGTH: 19
<212> TYPE: DNA
<213> ORGANISM: Rattus norvegicus
<220> FEATURE:
<221> NAME/KEY: STS
<222> LOCATION: (1)..(19)
<223> OTHER INFORMATION: Another PCR primer for cloning of the 5' end of
      IGFBP-3 gene from rat pancreas cDNA library
      The Sequence is described at page 38, line 23
      of the specification.
<300> PUBLICATION INFORMATION:
<301> AUTHORS: Shimasaki, S.
<303> JOURNAL: Biochem. Biophys. Res. Commun.
<304> VOLUME: 165
<306> PAGES: 907-
<307> DATE: 1989

<400> SEQUENCE: 4
tgctgatcac gttgttggc                                            19

<210> SEQ ID NO 5
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Description of Artificial Sequence:  Synthetic
      DNA oligomer which was used in preparation of [Leu27]rIGF-II
      The Sequence is described at page 45, line 24 of the
      specification.
```

```
<300> PUBLICATION INFORMATION:
<301> AUTHORS: SAKANO, K.
<303> JOURNAL: J. Biol. Chem.
<304> VOLUME: 266
<306> PAGES: 20626-
<307> DATE: 1991

<400> SEQUENCE: 5
ctggaaaaga ggaaacctct g                                               21

<210> SEQ ID NO 6
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Description of Artificial Sequence: Synthetic
      DNA oligomer which was used in preparation of [Leu43]rIGF-II
      The Sequence is described at page 45, line 24 of the
      specification.
<300> PUBLICATION INFORMATION:
<301> AUTHORS: SAKANO, K.
<303> JOURNAL: J. Biol. Chem.
<304> VOLUME: 266
<306> PAGES: 20626-
<307> DATE: 1991

<400> SEQUENCE: 6
ttcttcgagg atacctc                                                    17
```

COMPOSITION OF AN ENDOGENOUS INSULIN-LIKE GROWTH FACTOR-II DERIVATIVE

TECHNICAL FIELD

The present invention relates to compounds and methods for elevating endogenous insulin-like growth factors and their activities in living bodies.

BACKGROUND ART

Insulin-like growth factors (hereinafter "IGF") are found in two distinct molecular forms called IGF-I and IGF-II, respectively. Human IGF-I and IGF-II are 70 and 67 amino acids in length, respectively. Compared to IGF-II, IGF-I has three more amino acids at the site corresponding to the C peptide, which is a partial structure of insulin. The amino acid sequence homology between IGF-I and IGF-II is about 60% while that between IGF-I and insulin is about 40%. Although the liver and kidney are the major sites of production for IGF-I in living bodies, northern blot analysis of MRNA has revealed that IGF-I is produced by almost all tissues in the body (D'Ercole, A. J., et al., Proc. Natl. Acad. Sci. USA. 81, 935 (1984); Humbel, R. E., et al., Eur. J. Biochem., 190, 445 (1990)). IGF-I is considered to act not only as an endocrine factor but also as paracrine or autocrine factor.

IGF-I and IGF-II bind to distinct and specific receptors; an IGF-I receptor and an IGF-II/cation-independent mannose-6-phosphate receptor, respectively. However, since IGF-II has also been shown to bind to the IGF-I receptor, the various biological activities associated with IGF-II are thought to occur mainly through the IGF-I receptor located on cell surface (Casella, S. J., et al., J. Biol. Chem., 261, 9268 (1986); Sakano, K., et al., J. Biol. Chem., 266, 20626 (1991)).

The IGF-I receptor shares a high degree of amino acid sequence homology with the insulin receptor and the two molecules resemble each other in their intracellular signal transduction mechanism (Shemer, J., et al., J. Biol. Chem., 262, 15476 (1987); Myers, M. G. Jr., et al., Endocrinology, 132,. 1421 (1993)). IGFs regulate glucose metabolism predominantly in the peripheral tissue, which is different from insulin, as shown in animal model studies. The receptors for IGFs and insulin are differentially localized in tissues, and this may explain why the biological effect of IGFs in the body is distinguishable from insulin's effect (Laager, R., et al., J. Clin. Invest., 92, 1903 (1993)).

The blood of an average adult human contains about 100 nM of IGF and about 100 pM of insulin (Baxter, R. C., in Modern Concepts of Insulin-Like Growth Factors (Spencer, E. M., ed) pp.371, Elsevier Science Publishing Co., New York-Amsterdam (1991)). Most IGFs found in living bodies form complexes with an IGF-binding protein (hereinafter "IGFBP"). It appears that a specific binding protein exists for each IGF. The hypoglycemic effect of free IGF or unbound IGF is about 5 to 10% of that of insulin (Guler, H. P. et al., New Engl. J. Med., 317, 137 (1987)), indicating that insulin-like growth factors are at concentrations of about 50 to 100-fold greater than insulin (Baxter, R. C., in Modern Concepts of Insulin-Like Growth Factors (Spencer, E. M., ed) pp.371, Elsevier Science Publishing Co., New York-Amsterdam (1991)).

The World Health Organization has classified the disease, Diabetes mellitus, into roughly three categories on the basis of their distinct clinical patterns:

(1) Insulin-dependent diabetes mellitus (hereinafter "IDDM")

(2) Non insulin dependent diabetes mellitus (hereinafter "NIDDM")

(3) Other diabetes mellitus (derived from pancreato-pathy diseases or endocrinopathy)

A method for treating IDDM involves insulin therapy, while diet therapy, kinesitherapy, or treatment with an oral hypoglycemic agent or with insulin is mainly used in the treatment of NIDDM. In recent years, IGF-I therapy has been considered as an alternative treatment for insulin-dependent diabetes mellitus in cases where administration of insulin alone is not effective (Kuzuya, H., et al. Diabetes 42, 696 (1993)). Also for NIDDM, effects of IGF have been under investigation (Zenobi, P. D., et al., J. Clin. Invest., .90,. 2234 (1992); Moses, A. C., et al. , Diabetes, 45, 91(1996)).

Guler et al. observed that the intravenous injection of IGF-I into adult humans in an amount of 100 μg/kg resulted in the lowering of blood glucose levels with the lowest level occurring after 20 minutes (Guler, H. P., et al., New Engl. J. Med., 317, 137 (1987))

Takano et al. observed that hypoglycemic activity was observed in adult humans following the subcutaneous injection of IGF-I in an amount of 60 to 120 μg/kg, and that administration of IGF-I every 6 days in an amount of 100 μg/kg lowered the uric acid and creatinine levels in blood (Takano, K., et al., Endocrinol. Jpn., 37, 309. (1990)).

In addition, there are reports on the lowering of free fatty acid levels in blood (Turkalj. I., et al., J. Clin. Endocrinol. Metab., 75, 1186 (1992)), the lowering of neutral fats such as triglyceride (Turkalj. I., et al., J. Clin. Endocrinol. Metab. 75, 1186 (1992); Zenobi, P. D. , et al. , J. Clin. Invest., 90, 2234 (1992)), and the lowering in total cholesterol level (Zenobi, P. D., et al., Diabetologia 36, 465 (1993)). Increases in renal blood flow and glomerular filtration rate (Elahi, D., et al., in Modern Concepts of Insulin-Like Growth Factors (Spencer, E. M., ed) pp2l9, Elsevier Science Publishing Co., New York-Amsterdam (1991)), have been reported for IGF-I.

There is also a report that the administration of IGF-II was effective for intractable diabetes mellitus (Usara, A., et al., Diabetes, 44, Suppl. 1, 33A, 1995)). Results from animal model studies suggest the effectiveness of IGF-I in the reduction of conditions associated with stress including glucose metabolism at the time of hemorrhagic shock, the alleviation of side effects caused by sugar infusion (Unexamined Japanese Patent Publication (KOKAI) No. Hei 7-242565).

Administering IGF to animals has helped to identify the numerous biological activities of IGF including hypoglycemic activity, induction of proliferation, cell differentiation, and anobolic activity. Local administration of IGF-I to the injured peripheral nervous system results in the proliferation of non-neural cells while stimulating neurons. It is reported that IGF-I receptors are present on spinal cells and that administration of IGF-I decreases cell death of motor neurons. In addition, it is recognized that the administration of IGF increases the muscular end plate, promotes the functional recovery of a damaged sciatic nerve and prevents peripheral motor paralysis observed during chemotherapy (Sjoberg, J., et al., Brain Res. 485, 102 (1989).

Based on these foregoing experimental observations in the peripheral nervous sytem, clinical tests using IGF-I in the treatment of amyotrophic lateral sclerosis and degenerative diseases of the motor neuron have been conducted (Lewis, M. E., et al., Exp. Neurol., 124, 73(1993)).

Similarly, the use of IGF in promoting the survival of neuronal cells is recognized as being important in the treatment of Alzheimer's disease, apoplexy, amyotrophic lateral sclerosis, Parkinson's disease and the like (Unexamined Japanese Patent Publication (KOHYO) No. Hei 6-510305). In addition, the effectiveness of IGF-I in the treatment of muscular dystrophy has also been reported (Vlachopapadopoulou, E., et al., J. Clin. Endocrinol. Metab., 80, 3715 (1995)).

The effects of IGF on diabetic neuropathy have also been studied. In an IDDM rat model (STZ-rat: streptozotocin-diabetic rat model), alleviation of diabetic neuropathy was observed when IGF was administered at concentrations that did not lower blood glucose levels (Zhuang, H-X, et al., Exp. Neurol., 140, pp198–205 (1996)). It has also been reported that administration of IGF in an NIDDM rat model (diabetic obese Zucker (fa/fa) rat), reduced the level of IGF-II mRNA in the sciatic nerve, spinal nerves and brain nerves, and alleviated the diabetic neuropathy when used at a concentration that did not result in lowering of blood glucose levels (Zhuang, H-X, et al., J. Pharmacol. Exp. Ther., 283, pp366–374 (1997)). These findings suggest that IGF is effective in the treatment of diabetic neuropathy.

The effects of IGF have also been studied on cardiac function. When doxorubicin is administered to rats, it causes myocardiopathy, but administration of IGF-I improves myocardial function (Ambler, G. R., et al., Cardiovasc. Res., 27, 1368 (1993)). Consequently, IGF-I is thought to be useful in the prevention and treatment of myocardiopathies including myocarditis and myocardial infarction, cardiac disease, and acute attack via its ability to increase cardiac rate and improve cardiac output (Unexamined Japanese Patent Publication (KOHYO) No. Hei 6-504286).

The effects of IGF-I on acute renal insufficiency caused by ischemia have also been reported. On day 5 after an ischemic attack, IGF-I was administered three times daily by subcutaneous injection for three days. The result was that IGF improved renal function, promoted formation of new renal tubules, inhibited proteolysis and promoted protein synthesis, and decreased catabolism (Ding, H., et al., J. Clin. Invest., 91, 2281 (1993)).

It has also reported that the local administration of IGF-I to a skin injury, i.e., wounds, burn injuries or the like, reduces the length of recovery. In a burn injury model, the administration of rat IGF-I increased body weight, weight of the enteromucosa, mucosal DNA and protein expression, and decreased the transfer of enterobacterium to the intestinal lymph gland, thereby improving intestinal function and life prognosis (Huang, K. F., et al., Arch. Surg., 128, 47 (1993)).

Together with a platelet-derived growth factor (hereinafter "PDGF"), IGF-I promotes mitosis and protein synthesis of cultured mesenchymal cells, and although curing of skin disorders is not promoted by the single use of PDGF or IGF-I, the combined use of both factors promotes the growth of connective and epithelial tissues (Stiles, C. D., et al., Proc. Natl. Acad. Sci. USA, 76, 1279 (1987)). In another report, however, the single application of either one of these growth factors was shown to stimulate wound healing (Tsuboi, R., et al., J. Exp. Med., 172, 245 (1990)). Therefore, attempts have been made to use IGF for promoting wound healing (Unexamined Japanese Patent Publication (KOKAI) No. Sho 63-233925, Unexamined Japanese Patent Publication (KOHYO) Nos. Hei 3–505870 and Hei 6-506191, and Unexamined Japanese Patent Publication (KOKAI) No. Hei 7-316066).

In addition, IGF-I is effective at improving immune function. IGF-I is produced in the thymus and sites of inflammation and is considered to be important in the regulation of proliferation and function for T lymphocytes expressing the IGF-I receptor (Tapson, V. F., et al., J. Clin. Invest., 82, 950 (1988)). It is reported that IGF-I promotes the proliferation of lymphocytes at nanomolar concentrations (Schimpff, R. M., et al., Acta Endocrinol. 102, 21 (1983)). Accordingly, the use of IGF-I for treatment of immunodeficient patients including AIDS patients is under investigation (Unexamined Japanese Patent Publication (KOHYO) No. Hei 6-508830).

Moreover, IGF-I is considered to be effective in the treatment of osteoporosis since increases in bone mass have been associated with IGF (Bennett, A. E., et al., J. Clin. Endocrinol. Metab., 59, 701 (1984); Brixen, K., et al., J. Bone. Miner. Res., 5, 609 (1990); Johannsson, A. G., et al., J. Intern. Med., 234, 553 (1993); Johannsson, A. G., et al., Lancet, 339, 1619 (1992); Riggs, B. L., Am. J. Med., 95, Suppl.5A, 62S, (1993); Unexamined Japanese Patent Publication (KOKAI) No. Hei 4-235135 and U.S. Pat. No. 4,861,757).

However, it is recognized that in their naturally occurring state, almost all of the IGFs form complexes with IGFBP in living bodies, which effectively serves to regulate their physiological activity in vivo (Rechler, M. M., Vitam. Horm., 47, 1 (1993); Clemmons, D. R., Growth Regul. 2, 80 (1992)).

Six IGFBPs (designated "IGFBP-1 to IGFBP-6") have been identified thus far, and each of them exhibits a high degree of amino acid sequence identity or homology. The homology is markedly similar in the N-terminal and C-terminal regions where many of the cysteine residues are located, while the proteins are much less homologous in their intermediate domains. For all six human IGFBPs, the respective positions for sixteen (16) cysteine residues is conserved (IGFBP-1 to IGFBP-5 have conserved 18 cysteine residues) (Shimasaki, S., et al., Prog. Growth Factor Res., 3, 243 (1991)).

The concentrations of IGFBP-1, IGFBP-2 and IGFBP-3 in the blood of an adult human are about 2 nM, 5 nM and 100 nM, respectively, and IGFBP-3 is a major binding protein for IGF (Baxter, R. C., in Modern Concepts of Insulin-Like Growth Factors (Spencer, E. M., ed) pp371, Elsevier Science Publishing Co., New York-Amsterdam (1991)). When normal human serum is fractionated by gel filtration under neutral conditions, the IGFs elute in the vicinity of 150 kDa and are found as a ternary complex (Baxter, R. C., et al., Proc. Natl. Acad. Sci. USA, 86, 6898 (1989)). This ternary complex is composed of IGF-I (or IGF-II) (m.w. of about 7.5 Kda), IGFBP-3 (m.w. of 53 Kda and inert to acid) and a subunit protein (m.w. of 84 KDa and labile to acid (Acid Labile Subunit or "α-subunit"; hereinafter "ALS")). It is hypothesized, that when IGF binds to IGFBP-3, the major binding protein in blood, ALS binds to this binary complex to form a ternary complex having a total m.w. of 150 KDa.

It is considered that free IGF or a binary complex of IGF and IGFBP are able to pass through the capillary wall, while the ternary complex cannot (Rechler, M. M., Vitam. Horm., 47, 1(1993)). As regards the half-life of human IGF in blood, that of free IGF is as short as about 10 minutes, that of the binary complex of IGF and IGFBP is about 30 minutes and that of the ternary complex composed of IGF, IGFBP-3 and ALS is about 15 hours (Zapf, J., et al., in Modern Concepts of Insulin-Like Growth Factors (Spencer, E. M., et) pp.591, Elsevier Science Publishing Co., New York-Amsterdam (1991)).

As a result of the ternary complex formation, the half-life of IGF in blood is extended and its physiological activity is suppressed. Also, formation of a binary complex of IGF and IGFBP, extends the half-life of IGF in blood and is involved in the regulation of the physiological activity of IGF (Baxter, R. C., et al., Prog. Growth Factor Res., 1, 49 (1989)).

Little or no difference is observed in ALS among species, and homology of ALS between a human and a rat is 78% (Dai, J., et al., Biochem. Biophys. Res. Commun., 188, 304 (1992)). Earlier, it was reported that ALS alone does not bind to IGF or IGFBP-3, but more recently ALS has been shown to exist as a complex with IGFBP-3 in the serum of rats (Lee, C. Y., Endocrinology, 136, 4982 (1995)).

IGF administration to a living body does not elevate the concentration of free IGF in blood, but elevates the concentration of IGFBP-2. It is now considered that an IGF-dependent mechanism exists in the living body for regulating the expression of IGFBP (Zapf, J., et al., in Modern Concepts of Insulin-Like Growth Factors (Spencer, E. M., et) pp.591, Elsevier Science Publishing Co., New York-Amsterdam (1991)).

One regulatory mechanism associated with the ternary complex of IGF, IGFBP-3 and ALS is seen with non-islet cell tumor hyperglycaemia (hereinafter "NICTH"). Non-islet cell tumors, which produce IGF-II, are associated with hypoglycaemia or low blood glucose levels. NICTH-derived IGF-II is glycosylated in the E-domain of the precursor protein. Normally, IGF-II exists as a 7.5 kDa nonglycosylated protein.

Glycosylated IGF-II forms a complex with IGFBP-3, but cannot form a ternary complex with IGFBP-3 and ALS (Baxter, R. C., in Modern Concepts of Insulin-Like Growth Factors (Spencer, E. M., ed) pp371, Elsevier Science Publishing Co., New York-Amsterdam (1991)) so the glycolsylated form is considered to exert blood glucose lowering action because of its inability to form complexes with ALS. Glycosylated IGF-II is complexed with IGFBP-3 in blood, and this complex is thought to pass through the capillary vessel wall (Rechler, M. M., Vitam. Horm., 47, 1 (1993)) and to reach the target site. Administration of the IGF-I and IGFBP-3 complex to hypophysectomized rats, demonstrated IGF-I activity, although weaker than the administration of IGF-I alone (Zapf, J., et al., J. Clin. Invest., 95, 179 (1995)). On the basis of these results, the complex of IGF and IGFBP-3 found in blood, is presumed to be transported to target tissues or organs where the activity of IGF is demonstrated.

The IGF-IGFBP complex can also be regulated by a IGFBP-specific protease. IGFBP-3 concentrations in the blood of a gravida during the last stage of pregnancy are slightly increased when measured by a radioimmunoassy (hereinafter "RIA") using an anti-IGFBP-3 antibody. However, when blood samples from the same patient are analyzed by a western blot method using $^{125}$I-IGF, a decrease in IGFBP-3 concentration is observed. This apparent discrepency in results is explained by the presence of a protease found in the blood of the gravida, which specifically degrades IGFBP-3 (Hossenlopp, P., et al., J. Clin. Endocrinol. Metab., 71, 797 (1990); Giudice, L.C., et al., J. Clin. Endocrinol. Metab., 71, 806 (1990)). As a result of this proteolytic activity on the IGFBP-3 protein, the affinity between IGF and IGFBP-3 is lowered, and a direct increase in IGF activity is observed.

These observations demonstrate that activity of IGF in the living body is highly regulated by IGFBP and ALS. Exogenous IGF when administered is rapidly metabolized or complexed with IGFBP or ALS. Even if IGF or a compound having IGF-like activity is administered exogenously, the IGF activity is controlled by IGFBP and/or ALS in the living body.

The inventors have found that endogenous IGF can be increased by administering compounds which release IGF from binary (IGF-IGFBP) and ternary (IGF-IGFBP-ALS) complexes or which increase binary complex formation having IGF-like activity.

The compounds of the present invention have at least one the properties of: converting a binary IGF-IGFBP complex or a ternary IGF-IGFBP-ALS complex into free IGF; converting the ternary complex into the binary IGF-IGFBP complex; dissociating the ternary complex into IGF or the binary IGF-IGFBP complex; or inhibiting the formation of the binary IGF-IGFBP complex or the ternary IGF-IGFBP-ALS complex.

An object of the present invention is to utilize the abundant amount of endogenous IGF which is otherwise physiologically regulated by complexing with IGFBP and or ALS.

Another object of the invention is a method for elevating the concentration of IGF, comprising converting complexed IGF into free IGF.

Another object of the present invention is a method for elevating the concentration of the binary complex, which has lower IGF activity than free IGF but higher IGF activity than the ternary complex.

DISCLOSURE OF THE INVENTION

Biologically active, unbound IGF can be obtained by:

conversion of the IGF-IGFBP complex or IGF-IGFBP-ALS complex into IGF;

dissociation of IGF from the IGF-IGFBP complex or IGF-IGFBP-ALS complex; or inhibition of the binding of IGF and IGFBP or binding of IGF, IGFBP and ALS.

A biologically active complex of IGF-IGFBP can be obtained by:

conversion of the ternary complex to the binary complex;

dissociation of the binary complex from the ternary complex; or inhibition of the binding of the binary complex to ALS.

The concentrations of free IGF or the binary complex can be increased by:

1) a compound which coverts the binary complex in the living body into free IGF;

2) a compound which dissociates free IGF from the binary complex in the living body;

3) a compound which inhibits the binding of IGF and IGFBP in the living body;

4) a compound which converts the ternary complex in the living body into the binary complex;

5) a compound which dissociates the binary complex from the ternary complex in the living body;

6) a compound which inhibits the binding of the binary complex in the living body to ALS;

7) a compound which converts the ternary complex in the living body into free IGF;

8) a compound which dissociates [dissociates] IGF from the ternary complex in the living body;

9) a compound which inhibits the binding of IGF, IGFBP and ALS in the living body;

10) a compound which binds to IGFBP but does not bind to an IGF receptor or an insulin receptor;

11) an IGF derivative which binds to IGFBP but does not bind to an IGF receptor or an insulin receptor;

12) an IGF derivative having the addition, deletion or substitution of one or more amino acid residues, and which binds to IGFBP but does not bind to an IGF receptor or an insulin receptor;

13) an IGF derivative having an amino acid sequence similar to human IGF-II except that the tyrosine residue at amino acid position 27 and the valine residue at amino acid position 43 have been substituted with a leucine residue, and which binds to IGFBP but does not bind to an IGF receptor or an insulin receptor;

14) an anti-IGFBP antibody which binds to IGFBP but does not bind to an IGF receptor or an insulin receptor;

15) an anti-IGFBP antibody which binds to IGFBP-3 but does not bind to an IGF-I receptor or an insulin receptor.

Another aspect of the present invention is a medicament comprising a compound which can elevate the concentration of free IGF or the binary complex.

Another aspect of the present invention is a screening method for identifying a compound which can elevate the concentration of free IGF or the binary complex.

BEST MODE FOR CARRYING OUT THE INVENTION

Figure 1:
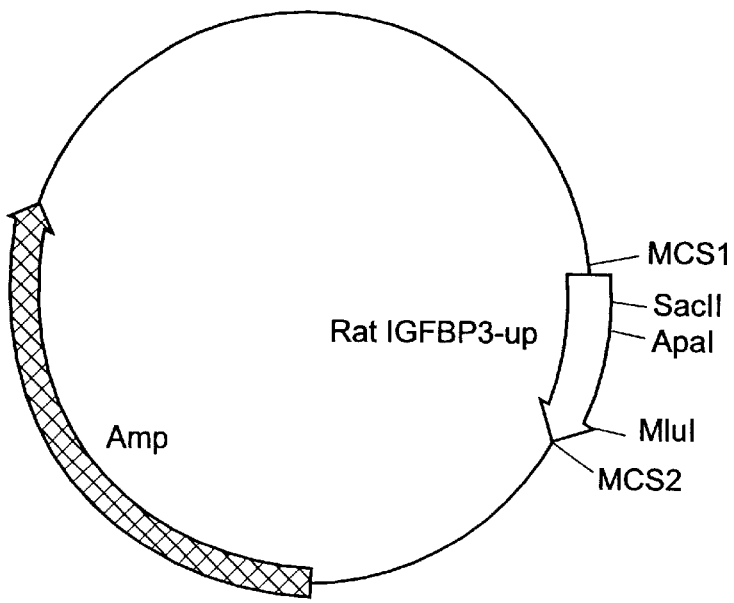
FIG. 1 illustrates the restriction map of plasmid BP-3 up/pUC19/Δ in which rat IGFBP-3 gene 5' end region is cloned.

A method for elevating the concentration of free IGF and a method for elevating a binary complex are described as follows.

The method for elevating the concentration of free IGF according to the present invention is achieved by utilizing free IGF or IGF existing in the form of a binary IGF-IGFBP complex and/or ternary IGF-IGFBP-ALS complex, all three forms of which occur endogenously in the living body.

The term "living body" as used herein means the blood, tissues or organs such as the liver or kidney of a human or mammals other than humans such as a cow, horse, sheep or pig.

The term "free IGF" as used herein means IGF which has been converted from or dissociated from a binary or ternary complex, or soluble IGF which is unbound or uncomplexed with IGFBP and/or ALS.

In the present invention, the concentration of free IGF is elevated by:

converting, in the binary IGF-IGFBP complex, inactive IGF to active IGF, dissociating IGF from the binary IGF-IGFBP complex, inhibiting the binding of IGF and IGFBP, converting, in the ternary IGF-IGFBP-ALS complex, inactive IGF to active IGF, dissociating IGF from the ternary IGF-IGFBP-ALS complex, inhibiting the binding of IGF to IGFBP and ALS, or the like.

It is also possible to elevate the concentration of free IGF by:

converting the ternary IGF-IGFBP-ALS complex to the binary IGF-IGFBP complex, dissociating the binary IGF-IGFBP complex from the ternary IGF-IGFBP-ALS complex, inhibiting the binding of the binary IGF-IGFBP complex to ALS, or by increasing the concentration of the binary IGF-IGFBP complex followed by:

converting the binary IGF-IGFBP complex to IGF, dissociating IGF from the binary IGF-IGFBP complex.

Since the method of the present invention increases the concentration of endogenous, biologically active IGF, the inventors envision the use of this free IGF in a method for the prevention and/or treatment of those diseases that are responsive to the action of IGF.

In the present invention, the concentration of the binary IGF-IGFBP complex is elevated by:

converting the ternary IGF-IGFBP-ALS complex into the binary IGF-IGFBP complex, dissociating the binary IGF-IGFBP complex from the ternary IGF-IGFBP-ALS complex, inhibiting the binding of the binary IGF-IGFBP complex to ALS, or the like.

The inventors have envisioned another method for the prevention and/or treatment of those diseases which are responsive to the IGF-like activity of the binary IGF-IGFBP complex.

The compounds of the present invention are described as follows.

The compounds of the present invention do not exhibit binding to the insulin receptor or the IGF receptor. The compounds are different from IGF or other IGF-like molecules.

The compound of the present invention which converts the binary IGF-IGFBP complex into IGF, acts on the binary complex, thereby converting it into IGF.

The compound of the present invention which dissociates IGF from the binary IGF-IGFBP complex, acts on the binary complex, thereby dissociating IGF.

The compound of the present invention which inhibits the binding of IGF and IGFBP, inhibits the formation of the binary IGF-IGFBP complex.

The compound of the present invention which converts the ternary IGF-IGFBP-ALS complex into the binary IGF-IGFBP complex, acts on the ternary complex, thereby converting it into the binary IGF-IGFBP complex.

The compound of the present invention which dissociates the binary IGF-IGFBP complex from the ternary IGF-IGFBP-ALS complex, acts on the ternary complex, thereby dissociating therefrom the binary IGF-IGFBP complex. The compound of the present invention which inhibits the binding of the binary IGF-IGFBP complex to ALS, inhibits the formation of the ternary IGF-IGFBP-ALS complex.

The compound of the present invention which converts the ternary IGF-IGFBP-ALS complex into IGF, acts on the complex, thereby converting it into IGF.

The compound of the present invention which dissociates IGF from the ternary IGF-IGFBP-ALS complex, acts on the ternary complex, thereby dissociating IGF.

The compound of the present invention which inhibits the binding of IGF, IGFBP and ALS, inhibits the formation of the ternary IGF-IGFBP-ALS complex, thereby increasing free IGF.

In the present invention, the binary IGF-IGFBP complex and ternary IGF-IGFBP-ALS complex are formed by static interaction, hydrogen bonding, hydrophobic interaction or the like. They include any kind of complex without particular limitation to the kind of IGF or IGFBP. Examples include a binary complex of IGF-I and IGFBP-3, a ternary complex of IGF-I, IGFBP-3 and ALS.

When the compound of the present invention is administered in vivo, free IGF or a binary IGF-IGFBP complex increase in a living body, resulting in biologically active IGF which may be used: as a medicament or used in a method for the prevention and/or treatment of diseases which are responsive to IGF.

The diseases that may be prevented or treated with the inventive compounds include at least one of diabetes mellitus, diabetic neuropathy, amyotrophic lateral sclerosis, and osteoporosis.

Selection of a compound for the prevention and/or treatment of a particular disease may depend on the tissue specific expression of IGFBP and/or tissue-specific effects of IGF. More specifically, a compound having a selective effect(s) on a particular organ such as muscle or bone, would be a preferred compound for the prevention or treatment of a muscle or bone disease responsive to IGF.

No particular limitations are placed on the compounds of the present invention except that they possess the activities as previously described. The compounds may be produced by organisms such as miroorganisms, plants and animals, or by cultured cells or tissues from plants or animals, or by extraction from organisms, or chemical synthesis. The compounds may be used alone or in combination.

The compounds of the present invention include insulin-like growth factor derivatives and anti-insulin-like growth factor-binding protein antibodies.

The term "insulin-like growth factor derivative" means a derivative of an insulin-like growth factor obtained by subjecting insulin-like growth factor to chemical modification or the like. A derivative may have the addition, deletion or substitution of one or more amino acid residues produced by the genetic engineering methods. The addition, deletion or substitution of an amino acid residue can be carried out by any one technique such as that described in the following reference (Genetic Engineering, 3, 1 (1981); Nucleic Acid Research, 10, 6487 (1982)).

Preferred examples of the insulin-like growth factor derivative of the present invention include a derivative obtained by substituting the tyrosine residue at amino acid position 27 and the valine residue at amino acid position 43 in the sequence for human insulin-like growth factor-II with a leucine residue.

The compound of the present invention may be administered either parenterally or orally, but oral administration is the preferred route of administration. The compounds of this invention can be formulated into various pharmaceutical compositions in a manner commonly employed in the art. Pharmaceutical compositions can contain additives such as excipients, disintegrators, binders, lubricants, fluidity improvers, dispersants, suspending agents, emulsifiers, antiseptics or stabilizers as needed.

Typical dosage forms for parenteral administration include ointments, plasters, suppositories, injections, eye drops, nose drops, ear drops, inhalants, spirits, cataplasms, liniments and lotions. Examples of the dosage forms for oral administration include elixirs, capsules, granules, fine granules, pills, suspensions, emulsions, powders, tablets, syrups, troches, dry syrups and lemonade.

The dosage of the pharmaceutical composition containing the compound of the present invention may be determined on the basis of the route of administration, the particular disease being be treated, the condition of the patient and the like.

The present inventors have identified two compounds, which elevate the level of free IGF-I in blood and increase IGF activity in a normal rat and a diabetic rat model. The compounds include an IGF-II derivative and anti-IGF-II antibodies, described hereinafter.

A description of a method for screening a compound of the present invention is the following.

A compound of the present invention can be identified by labeling any one of IGF, IGFBP and ALS (i.e. a labeled factor) for use in a direct or indirect method of detection, and determining whether the binding of the labeled factor (e.g., IGF) to an unlabeled factor (e.g., IGFBP) is inhibited by the compound or whether the compound can dissociate the labeled factor from a binary or ternary complex.

In a direct method, the amount of the labeled factor can be detected by appropriate physical measurement. For example, a factor labeled with a radioisotope can be detected directly by the measurement of radioactivity. A Scintillation Proximity Assay (Cook, N. D., Drug Discovery today, 1, 287 (1996)) or a similar method may also be used. When labeling is carried out with a color agent or fluorescent dye, the amount of the labeled factor can be detected by optical measurement.

In the indirect method, the factor is labeled with a nondetectable agent, which through a chemical reaction, forms a directly detectable molecule (e.g., dye, fluorescence dye) in a stoichiometric amount. For example, where a factor is conjugated to an enzyme, an enzyme substrate is added to produce a detectable dye following the reaction in the presence of a test compound.

Radioisotopic measurements can be carried out in accordance with art-recognized liquid phase methods. For example, after reaction of $^{125}$I-labelled IGF ($^{125}$I-IGF) with IGFBP, complex-bound $^{125}$I-IGF can be separated from unbound $^{125}$I-IGF by:

1) activated charcoal (Moses, A. C., et al., Endocrinology, 104, 536 (1979); Binoux, M., et al., J. Clin. Endocrinol. Metab 59 453 (1984); Scott, C. D., et al., Endocrinology, 116, 1094 (1985); Szabo, L., et al., Biochem. Biophys. Res. Commun., 151, 207 (1988); Gelato, M. C., et al., J. Clin. Endocrinol. Metab., 70, 879 (1990); Oh, Y. , et al. , Biochem. J. , 278, 249 (1991), etc.), 2) a lectin protein recognizing the sugar chain portion of IGFBP (Martin, J. L., et al., J. Biol. Chem., 261, 8754 (1986)), 3) immunoprecipitation using a primary and secondary antibody (Martin, J. L., et al., J. Biol. Chem. 261, 8754 (1986); Baxter, R. C., et al., J. Biol. Chem., 264, 11843 (1989); Baxter, R. C., Biochem. J., 271, 773 (1990) or the like).

Using any one of the above-described methods with $^{125}$I-IGF, $^{125}$I-IGFBP or $^{125}$I-ALS and an appropriate primary antibody, it is possible to evaluate the formation of the binary IGF-IGFBP complex or ternary IGF-IGFBP-ALS complex in the presence of a test compound.

These methods may not be suitable for the screening of multiple test compounds because of the extreme caution that must be taken in handling of radioisotopes having a short half-life and the centrifugation steps required in the separation method.

For the rapid screening of multiple test compounds, the Scintillation Proximity Assay may be more appropriate. Alternatively, non-radioisotopic, solid phase methods using an enzyme as a labeling agent can be used conveniently.

The screening of the compound of the present invention which converts the binary IGF-IGFBP complex into free IGF or dissociates free IGF from the binary IGF-IGFBP complex can be carried out, for example, by adding an enzyme-labeled IGF to immobilized IGFBP in the presence of a test compound, reacting, washing and then measuring the amount of bound enzyme activity. Alternatively, it is possible to immobilize IGF and label IGFBP with an enzyme.

The compound of the present invention, which inhibits the binding of IGF and IGFBP can be screened by simultaneously adding enzyme-labeled IGF and a test compound to an immobilized IGFBP, reacting, washing and then measuring the amount of bound enzyme activity. Alternatively, it is possible to immobilize IGF, label IGFBP with an enzyme and measure the activity of the enzyme.

The compound which converts the ternary IGF-IGFBP-ALS complex into the binary IGF-IGFBP complex, the compound which dissociates the binary IGF-IGFBP complex from the ternary IGF-IGFBP-ALS complex, the compound which converts the ternary IGF-IGFBP-ALS complex into free IGF or the compound which dissociates IGF from the ternary IGF-IGFBP-ALS complex, each according to the present invention, can be screened, for example, by adding IGF and enzyme-labeled IGFBP to immobilized ALS in the presence of a test compound, reacting, washing and then measuring the amount of bound enzyme activity. Alternatively, IGF can be labeled with an enzyme.

The screening may be carried out by adding enzyme-labeled ALS to an immobilized binary IGF-IGFBP complex to form the ternary complex, adding a test compound, reacting, washing and then measuring the amount of bound enzyme activity.

Screening may also be carried out by adding IGFBP and enzyme-labeled ALS to immobilized IGF to form the ternary complex, adding a test compound, reacting, washing and then measuring the amount of bound enzyme activity.

To identify those compounds which: convert the ternary IGF-IGFBP-ALS complex into the binary IGF-IGFBP complex; dissociate the binary IGF-IGFBP complex from the ternary IGF-IGFBP-ALS complex; convert the ternary IGF-IGFBP-ALS complex into free IGF; or dissociate free IGF from the ternary IGF-IGFBP-ALS complex, it is possible to employ the above-described screening method for the compound which converts the binary IGF-IGFBP complex into free IGF or the compound which dissociates free IGF from the binary complex.

The compound which inhibits the binding of the binary IGF-IGFBP complex to ALS or the compound which inhibits the binding of IGF, IGFBP and ALS, each according to the present invention, can be screened by simultaneously adding the binary complex (complex of IGF and enzyme-labeled IGFBP) in the presence of a test compound to immobilized ALS, reacting, washing and then measuring the amount of bound enzyme activity. Alternatively, it is possible to label IGF with an enzyme.

It is also possible to carry out screening by adding enzyme-labeled ALS in the presence of a test compound to an immobilized binary complex (IGF and IGFBP), reacting, washing and then measuring the amount of bound enzyme activity.

It is also possible to carry out screening by adding IGFBP, enzyme-labeled ALS and a test compound to immobilized IGF, reacting, washing and then measuring the amount of bound enzyme activity.

The screening methods used to identify those compounds which inhibit the binding of IGF and IGFBP may be used to confirm the identity of those compounds which inhibit the binding of the binary IGF-IGFBP complex to ALS or which inhibit the binding of IGF, IGFBP and ALS.

The immobilization of IGF, IGFBP or ALS may be achieved by any suitable art-recognized method. In both the direct and indirect solid-phase methods, immobilization may be achieved by any one of the following including avidin-biotin, hapten-anti-hapten antibody or the like. Examples of the solid phase material include glass, plastics such as polystyrene, polyacrylamide and cellulose acetate. The solid phase may be in the form of a test tube, bead, microtiter plate, disc, chip and the like. For screening of multiple sample specimens, a commercially available multi-well microtiter plate is preferred.

The enzymatic activity may be measured by known methods, which are dependent on conditions such as substrate, buffer, pH, temperature, etc. Examples of the enzymatic methods include colorimetry, fluorescence and luminescence.

IGF, IGFBP or ALS may be labeled with an enzyme by art-recognized methods and examples include a maleimide method, a periodic acid method and a glutaraldehyde method.

The selection of an enzyme used for labeling and an appropriate substrate may be considered as needed. For example, when β-D-galactosidase is used as an enzyme, examples of the substrate include 2-nitrophenyl-β-D-galactoside, 4-methylumbelliferyl-β-D-galactoside and 5-bromo-4-chloro-3-indolyl-β-D-galactoside. When peroxidase is used as an enzyme, examples of the substrate include 2,2'-azino-bis(3-ethylbenzthiazoline-6-sulfonic acid), 3,3',5, 5'-tetramethylbenzidine and 1,2-phenylenediamine. When alkaline phosphatase is used as an enzyme, examples of the substrate include 4-methylumbelliferyl phosphate and N-nitrophenyl phosphate.

Screening is preferably carried out in a buffer solution. Any buffer generally recognized for its use in the measurement of enzyme activity is appropriate. Examples include sodium phosphate buffer, glycine-sodium hydroxide buffer and Tris-HCl buffer solution. The pH of the buffer may be adjusted as appropriate, but is preferably 6.0 to 7.4 since the solubility of IGFBP is pH-dependent. Buffers may also be supplemented with a salt or surfactant. For example, when sodium chloride is added, a concentration up to 0.15 M is preferred.

INDUSTRIAL APPLICABILITY

According to the method of the present invention, IGF activity can be expressed or increased in vi vo, by converting endogenous IGF into free IGF or a binary IGF-IGFBP complex.

The in vivo administration of a compound of the present invention elevates the concentration of free IGF thereby increasing the biological activity of IGF. Accordingly, the compound of the present invention may be useful in the prevention and/or treatment of diseases such as diabetes mellitus, amyotrophic lateral sclerosis, osteoporosis and the like, or those diseases which are responsive to IGF.

The present invention is described in more detail by the following Examples and is not in any way limited by the Examples.

EXAMPLES

Example 1

Preparation of Human IGF-I and IGF-II

Human IGF-I was purchased from GroPep Pty. Ltd. Human IGF-II was obtained in a similar manner to that of Sakano, et al. (Sakano, K., et al., J. Biol. Chem., 266, 20626 (1991)). Specifically, human IGF-II was expressed in *Escherichia coli* by a recombinant gene technique. The human IGF-II protein was extracted from cells, refolded and purified by chromatography on a reverse-phase HPLC column.

Example 2

Cloning of Rat IGFBP-3 Gene

The rat IGFBP-3 gene was cloned in accordance with the literature (Shimasaki, S., et al., Biochem. Biophys. Res. Commun., 165, 907 (1989)). PCR primers were used to amplify the 5' and 3' ends of the IGFBP-3 gene from a rat pancreas cDNA library.

The sequences of the 5' primers were as follows:

5'-CGCCATGCATCCCGCGCGCC-3' (SEQ I.D. No. 1) and

5'-ACGCCGCACGCGTCGCCTTC-3' (SEQ I.D. No. 2)

The sequences of the 3' primers were as follows:

5'-GCGCGGGCCCCGTGGTGCGCTGCGAACCGT-3' (SEQ I.D. No. 3) and

5'-TGCTGATCACGTTGTTGGC-3' (SEQ I.D. No. 4)

The PCR fragments were blunt-ended, phosphorylated, and inserted into a pUC19 vector (SalI/Blunting/BAP), followed by subcloning of the 5' fragment (5' end BP-3 up/pUC19) and the 3' fragment (3' end: BP-3 down/pUCl9) into the vector.

The SphI site located upstream from the transcription initiating codon (ATG) of the 5' BP-3 up/pUIC19 clone was eliminated to generate 5'. BP-3 up/pUC19/ΔSphI (refer to FIG. 1).

Figure 2:
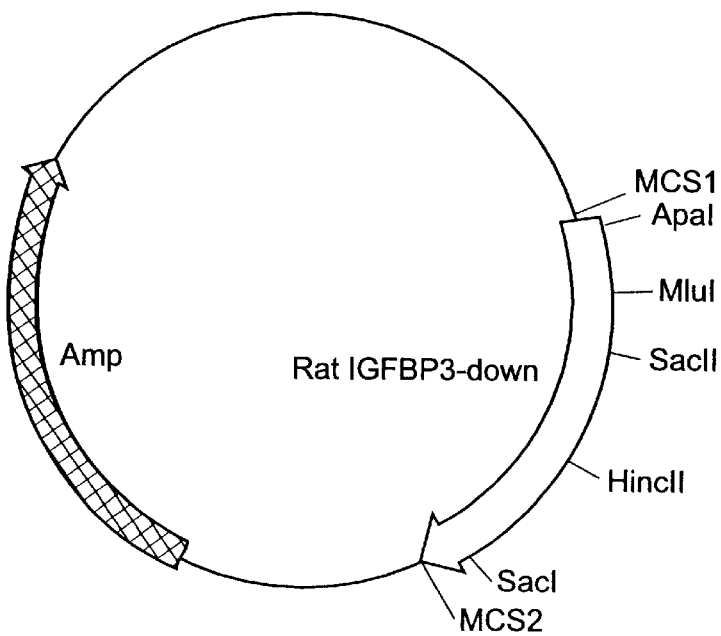
FIG. 2 illustrates the restriction map of plasmid BP-3 down/pTV119N in which rat IGFBP-3 gene 3' end region is cloned.

After digestion of the 3' BP-3 down/pUIC19 clone with BamHI-PstI, the fragment containing BP-3 down was recovered, blunt-ended, and inserted into pTV119N (HincII/BAP) containing a lacZ promoter to generate 3' BP-3 down/pTV119N (refer to FIG. 2).

Figure 3:
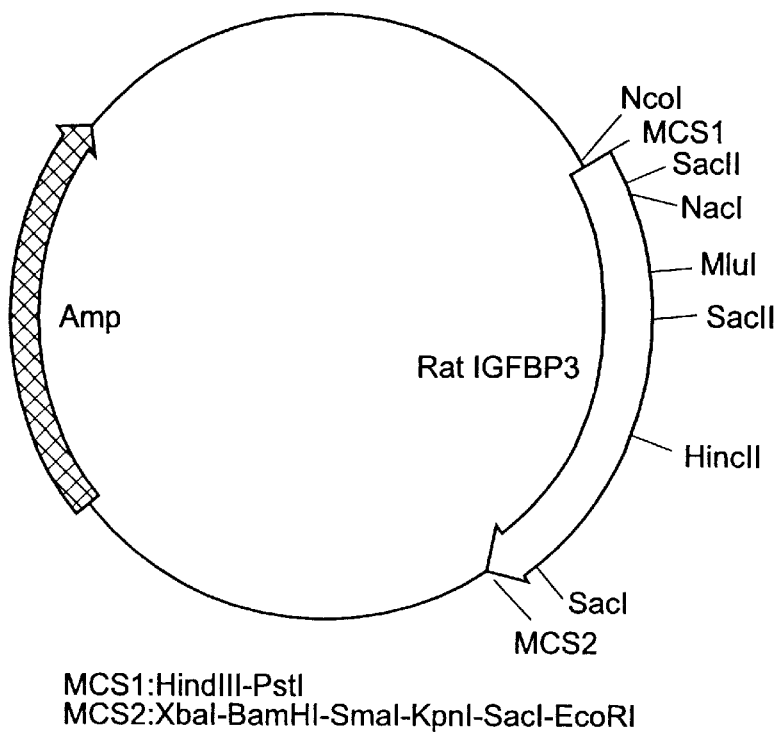
FIG. 3 illustrates the restriction map of plasmid BP-3/pTV119N in which rat IGFBP-3 is cloned.

The 5' end clone (BP-3 up/pUC19/ΔSphI) was digested with M1uI/HindIII, and a 250 bp fragment containing BP-3 up was recovered. The 3' end clone (BP-3 down/pTV119N) was treated with M1uI/HindIII/BAP followed by subcloning of the 250 bp fragment containing BP-3 up in order to generate a rat IGFBP-3 clone designated BP-3/pTV119N (refer to FIG. 3).

Example 3

Construction of Vector for the Expression of Rat IGFBP-3 Gene in Animal Cells

Figure 4:
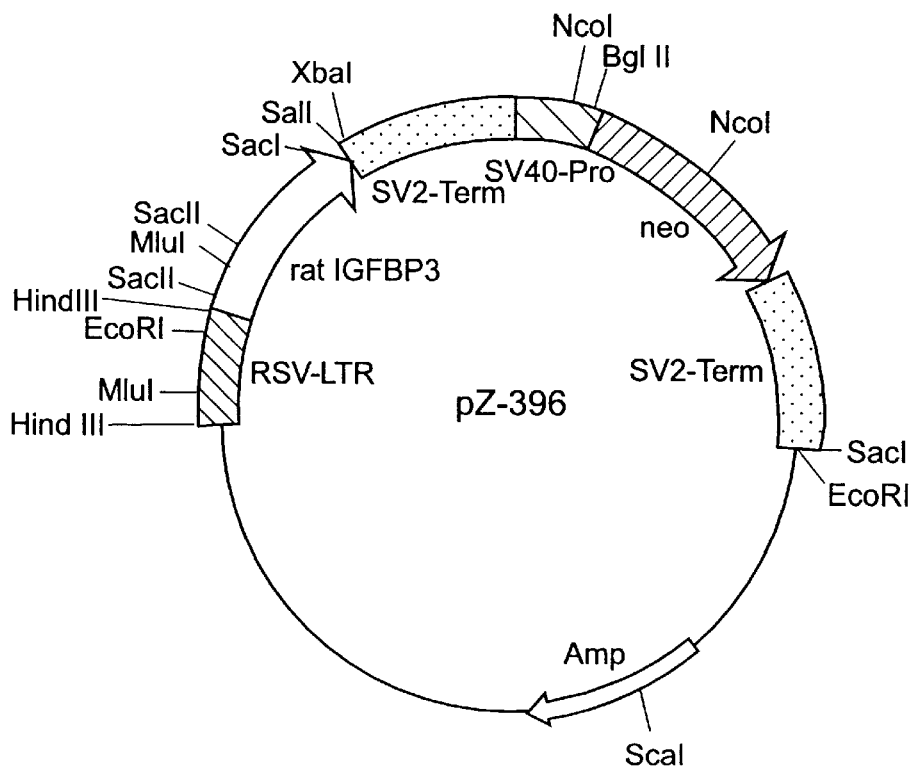
FIG. 4 illustrates the restriction map of lasmid RSV-LTR/rat IGFBP-3/SV2-Term/SV40-Pro/neo/SV2-Term/+Amp which is a rat IGFBP-3 expression vector in animal cells.

The rat IGFBP-3 clone was inserted into a plasmid containing the RSV-LTP (Rous sarcoma virus long terminal repeat) (Nawa, K., et al., Biochem. Biophys. Res. Commun., 171 729 (1990)) for expression of the protein in animal cells. The BP-3/pTV119N plasmid was digested with XbaI/HindIII to release a 900 bp fragment. The fragment was inserted into an expression plasmid (SV2-Term/SV40-Pro/neo/SV2-Term/+Amp), followed by subcloning into the HindIII site of an approximate 600 bp fragment of RSV-LTR obtained by HindIII digestion (RSV-LTR/rat IGFBP-3/SV2-Term/SV40-Pro/neo/SV2-Term/+Amp) (refer to FIG. 4).

Example 4

Construction of Vector for the Expression of Rat IGFBP-3 Gene in *E. coli*

Figure 5:
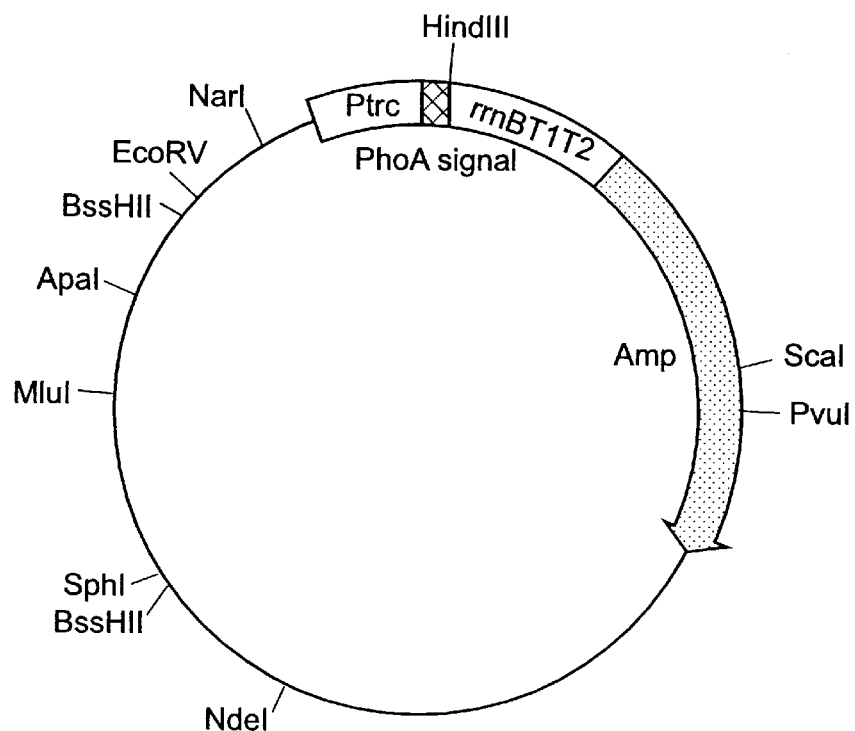
FIG. 5 illustrates the restriction map of the secretory expression vector used in the preparation of an expression vector for *E. coli*.

For expression in *Escherichia coli*, a secretory expression plasmid containing a PhoA signal sequence was used. The PhoA signal sequence was prepared with a synthetic DNA oligomer, and inserted into the NcoI/HindIII cut site of the expression plasmid, pTrc99A (product of Pharmacia Biotech AB) (refer to FIG. 5). In order to express the rat IGFBP-3 protein in *E. coli*, it was necessary to delete the rat signal sequence from the clone by cutting the BP-3/pTV119 plasmid with NaeI/XbaI (Example 2).

Figure 6:
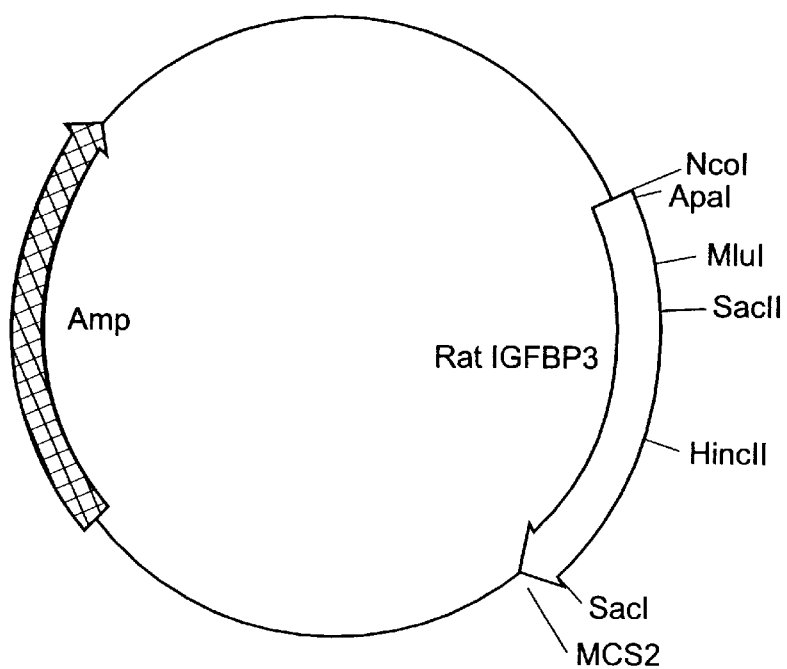
FIG. 6 illustrates the restriction map of a plasmid containing a rat IGFBP-3 gene fragment from which the signal sequence has been removed.

The resulting fragment was inserted into the plasmid BP-3/pTV119 previously treated with NcoI/Klenow/XbaI/BAP, whereby the plasmid shown in FIG. 6 was prepared.

Figure 7:
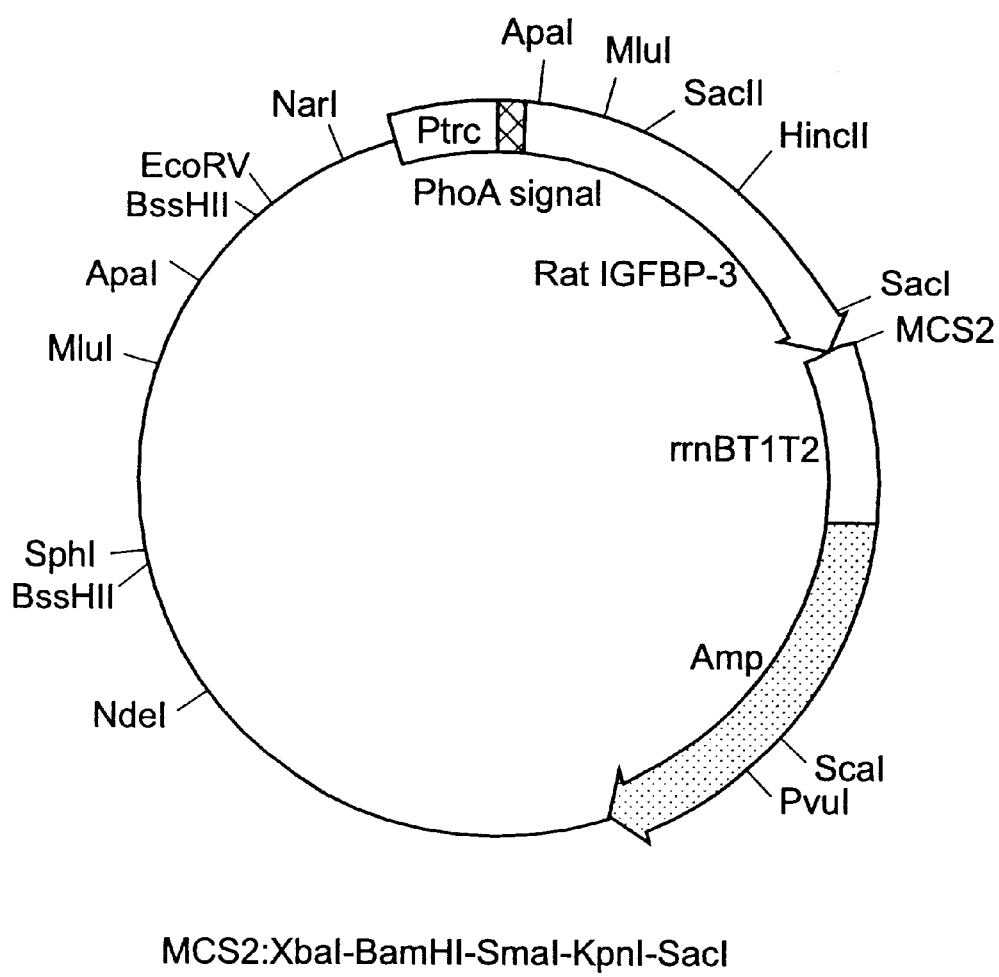
FIG. 7 illustrates the restriction map of a plasmid which is a rat IGFBP-3 secretory expression vector in *E. coli*.

Since the plasmid had an NcoI site, it was necessary to cut with NcoI/EcoRI and blunt-end with Mung Bean Nuclease, to recover the rat IGFBP-3 gene fragment from which the signal sequence had been eliminated. The resulting fragment was inserted into the secretory expression vector (HindIII/Klenow/BAP) of FIG. 5 to prepare the secretory expression plasmid of rat IGFBP-3 (refer to FIG. 7).

Example 5

Expression of Rat IGFBP-3 in CHO-K1 Cells and Purification Thereof

Rat IGFBP-3 was expressed in CHO-K1 cells. The plasmid of FIG. 4 was transfected into CHO-K1 cells by the calcium phosphate method. Recombinant cells were cloned in DMEM/F-12 medium containing 0.4 mg/ml G-418, selected and subsequently cultured in T medium containing 1% ITES. Culture supernatants were collected and an enzyme inhibitor (2 mM benzamide/1 mM PMSF/100 U/ml Trasylol /2 mM EDTA) was added. The mixture was sterile filtered ("CAPSULE FILTER 0.2 µm sterilized"; product of Gelman Science), and the pH adjusted to 6.0 with a solution of 1 M sodium acetate. The mixture was then applied to "SP-SEPHAROSE™ F.F. column" (product of Pharmacia Biotech AB) equilibrated with a 10 mM sodium acetate buffer (pH 6.0) containing 0.15 M sodium chloride. After successive washes with the same buffer and a buffer containing 0.5 M sodium chloride, elution was carried out with a buffer containing 1 M sodium chloride. The eluate was diluted two-fold and adjusted to a final pH of 7.0 with a sodium phosphate solution.

A ligand affinity column ("HiTrap affinity column, NHS-activated" (product of Pharmacia Biotech AB)), on which IGF-II had been immobilized, was prepared in a conventional manner.

After the column was equilibrated with a 50 mM sodium phosphate buffer (pH 7.0) containing 0.45 M sodium chloride, the SP-SEPHAROSE™ F.F. elution sample obtained above was applied. After washing successively with the same buffer, a 10 mM sodium acetate buffer (pH 7.0) containing' 1 M sodium chloride and water, elution was carried out with 0.5 M acetic acid. The eluate thus obtained was recovered, lyophilized, dissolved in 0.1% trifluoroacetic acid (hereinafter "TFA") and then subjected to reverse phase HPLC.

Rat IGFBP-3 (hereinafter "RBP-3CHO") was isolated on a reverse phase HPLC column ("CAPCELLPAK C18 SG300", 250×4.6 mm I.D., Shiseido Co., Ltd) using a linear gradient of acetonitrile at a flow rate of 1 ml/min, followed by lyophilization and storage.

Example 6

Expression of Rat IGFBP-3 in *E. coli* and Purification Thereof

*E. coli* clones expressing rat IGFBP-3 were cultured in LB medium at 37° C. with shaking at 250 rpm. When an absorbance of O.D.=3.45 was reached, IPTG was added to a final concentration of 0.3 mM, to induce protein expression. The cells were collected, and the periplasma was recovered by an osmotic shock method (Nossal, N. G. et al., J. Biol. Chem., 241, 3055 (1966)), followed by adjustment of the pH to 7.2 with a phosphate buffer.

The cell lysate was applied to an IGF-II affinity column to isolate the rat IGFBP-3 protein according to the method described in Example 5. The protein fraction was eluted with 0.5 M acetic acid followed by lyophilization. The lyophilizate was dissolved in 10 ml of 0.1% TFA and rat IGFBP-3 was eluted with an acetonitrile linear gradient at a flow rate of 1 ml/min on a reverse-phase HPLC column ("YMC-PACK PROTEIN-RP", 250×4.6 mm I.D., product of YMC Corporation. Rat IGFBP-3 (hereinafter "RBP-3 *E. coli*") obtained in this manner was lyophilized and stored.

Example 7

Purification of Rat ALS from Rat Serum

Rat ALS was purified from rat serum by a similar method to that of Baxter, et al. (Baxter, R. C., et al., Endocrinology, 134, 848 (1994)).

The above-described IGFBP-3 (RBP-3 *E. coli*) of Example 6 was immobilized on the affinity column of Example 5, on which IGF-II had been immobilized, to prepare an affinity column for isolation of rat ALS.

The final purification step was performed on a "DEAE-5PW column" (75×7.5 mm I. D., TOSOH CORPORATION) by equilibrating the column with a 10 mM sodium phosphate buffer (pH 8.0) containing 50 mM sodium chloride. Rat ALS (hereinafter "RALS") was eluted with a sodium chloride linear gradient in the same buffer, followed by lyophilization and storage.

Example 8

Preparation of Human IGF-II Derivative ([Leu27, Leu43] rIGF-II)

Human [Leu 27] rIGF-II and human [Leu 43] rIGF-II bind to the IGF-II/cation-independent mannose-6-phosphate receptor but exhibit almost no binding to the IGF-I receptor or the insulin receptor. As a consequence of the single amino acid substitutions in each of the derivatives, these molecules have a significantly lowered effect on cell proliferation (Sakano, K., et al., J. Biol. Chem., 266, 20626 (1991)). Furthermore, it is known that the binding of these derivatives to IGFBP-3 is almost similar to the wild type (Bach, L. A., et al., J. Biol. Chem., 268, 9246 (1993)).

In view of the foregoing, the present inventors developed a derivative ([Leu27, Leu43]rIGF-II) having two leucine residue substitutions (tyrosine at amino acid residue 27 and valine at amino acid residue 43 were each replaced with leucine), which exhibits little or no binding to the IGF-I receptor and the insulin receptor but which has affinity for IGFBP-3.

The derivative ([Leu27, Leu43] rIGF-II) was prepared in accordance with the Sakano method of preparation of human IGF-II (Sakano, K., et al., J. Biol. Chem., 266, 20626 (1991)).

A plasmid encoding [Leu27, Leu43] rIGF-II was constructed by a standard mutagenesis technique using human IGF-II DNA and two synthetic oligonucleotides (5'-CTGGAAAAGAGGAAACCTCTG-3' (SEQ I.D. No. 5), and 5'-TTCTTCGAGGATACCTC-3' (SEQ I.D. No. 6)). The mutant IGF-II were expressed in *E. coli* and purified.

Example 9

Preparation of Anti-Rat IGFBP-3 Antibody

Antibodies to the RBP-3CHO antigen (rat IGFBP-3 obtained in Example 5) were obtained by immunizing rabbits (Japanese white house rabbit, male, 5 in number). A total of 5 injections were administered at 2-week intervals.

The anti-serum was diluted two-fold with PBS, adjusted to pH 7.4 and applied to a Protein A column ("PROSEP-A", product of Bioprocessing Co.) equilibrated with PBS. After washing with PBS, elution was carried out with a 0.1 M glycine-hydrochloric acid buffer (pH 3.0). The eluate was concentrated by ultrafiltration and buffered with PBS. Altogether, five lots of polyclonal antibodies (anti-RBP-3 pAb #35, #36, #88, #89, #90) were obtained.

Example 10

Binding of IGF and IGFBP-3 in a Solid-Phase System

Materials:

A 96-well microtiter plate manufactured by Costar Corp.; 50 mM sodium phosphate buffer (pH 6.5) as a basic buffer for immuobilization; basic buffer supplemented with 0.03% Tween 20, basic buffer supplementee with 1% BSA and basic buffer supplemented with 0.25% BSA an 0.03% Tween 20 were used in the washing, blocking and binding steps, respectively. After each reaction, wells were washed twice with 400 µl/well of buffer. Horseradish peroxidase-labeled IGF-II (hereinafter "HRP-IGF-II") was prepared using a commercially available kit (PIERCE Chemichal Company).

The above-described materials are also used in Examples 11 to 17, unless otherwise specified.

Method:

To the microtiter plate, RBP-3 E. coli (150 ng/ml) was added in an amount of 50 µl/well and allowed to stand overnight at 4° C. for immobilization. After blocking, 50 µl/well of HRP-IGF-II (final concentration diluted 12,000-fold) was added at 25° C. for 2 hours in the presence or absence of a test compound. Test compounds at various concentrations were added to each well in a total volume of 50 µl.

In the final step, a solution of 2,2'-azino-bis(3-ethylbenzthiazoline-6-sulfonic acid) (hereinafter "ABTS"; Kirkegaard & Perry Laboratories) was added to each well (100 µl/well) and allowed to stand at room temperature. The absorbance (O.D.) at 405 nm was measured on a plate reader ("VMAX™", Molecular Devices).

The absorbance in the absence of a test compound is designated "$B_0$", and in the presence of a test compound is designated as "B". The absorbance in the absence of both a test compound and using a non-immobilized well (a well not containing RBP-3 E. coli) is designated as nonspecific bound (NSB). The percent binding of labeled IGF-II to immobilized IGFBP-3 in the presence of a test compound is calculated from the following equation:

$$(B-NSB)/(B_0-NSB) \times 100$$

Figure 8:
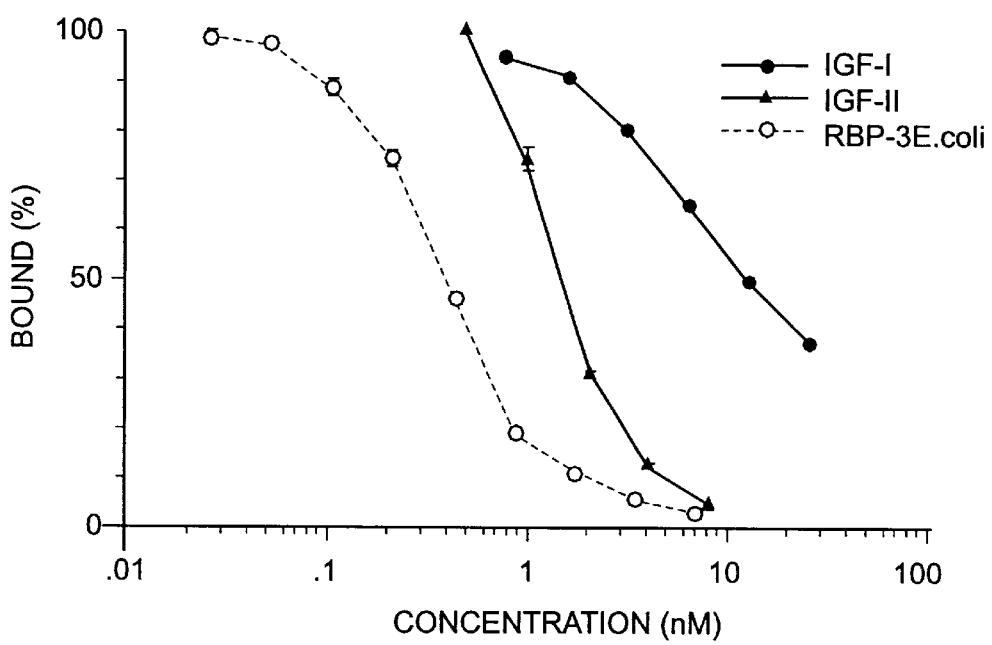
FIG. 8 illustrates the affinity of IGF-I and IGF-II for rat IGFBP-3 (RBP-3 *E. coli*) and the affinity of RBP-3 *E. coli* for IGF-II (Example 10).

The binding reactions for each of the test compounds, was performed triplicate. The average value is plotted and the SD value is indicated with a bar (refer to FIG. 8).

The above-described binding assay makes it possible to evaluate the affinity of various IGF and IGFBP derivatives for IGFBP and to screen for competitive inhibitors of IGF/IGFBP binding.

Example 11

Inhibition of IGF and IBFBP-3 Binding by Competitive Inhibitors

A competitive binding assay was performed in accordance with Example 10, using the test compounds set forth in Table 1. Each compound was dissolved or suspended in basic buffer containing 5% methanol at a final concentration of 1 mg/ml. The resulting solution or suspension was diluted with the reaction buffer 5-fold or to a final concentration of 200 µg/ml. The final concentration of each compound at the time of measurement was 100 µg/ml.

The percent binding of IGF-II to IGFBP-3 (RBP-3 E. coli) in the presence of a test compound was calculated using the following formula:

"percent total bound (100(%))–percent actual bound (%)"=percent inhibitory activity (%) of the test specimen.

Figure 9A:
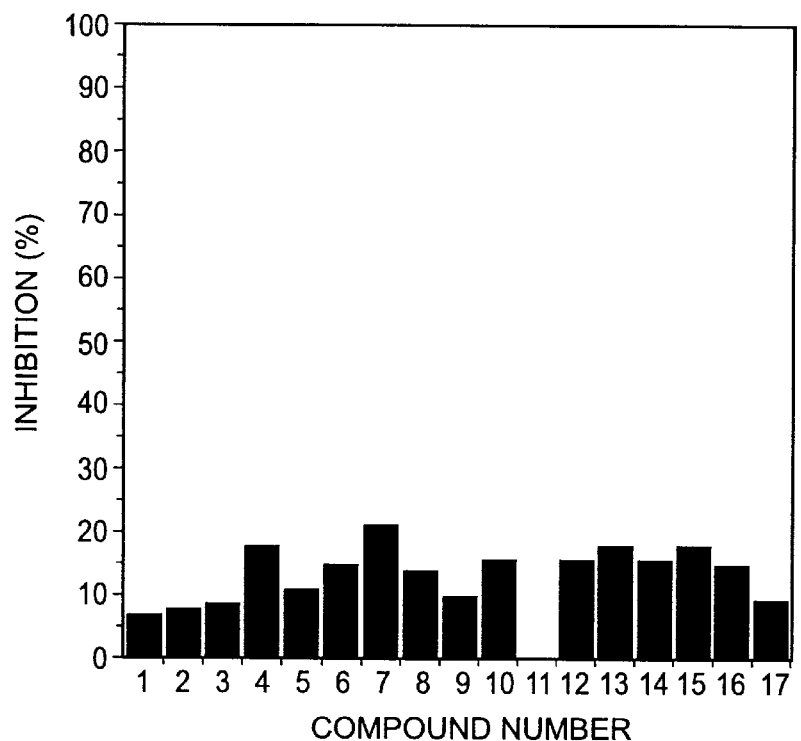
FIGS. 9A and 9B illustrate the inhibitory activity of various compounds (Table 1) against the binding of IGF-I and IGFBP-3 (Example 11).
Figure 9B:
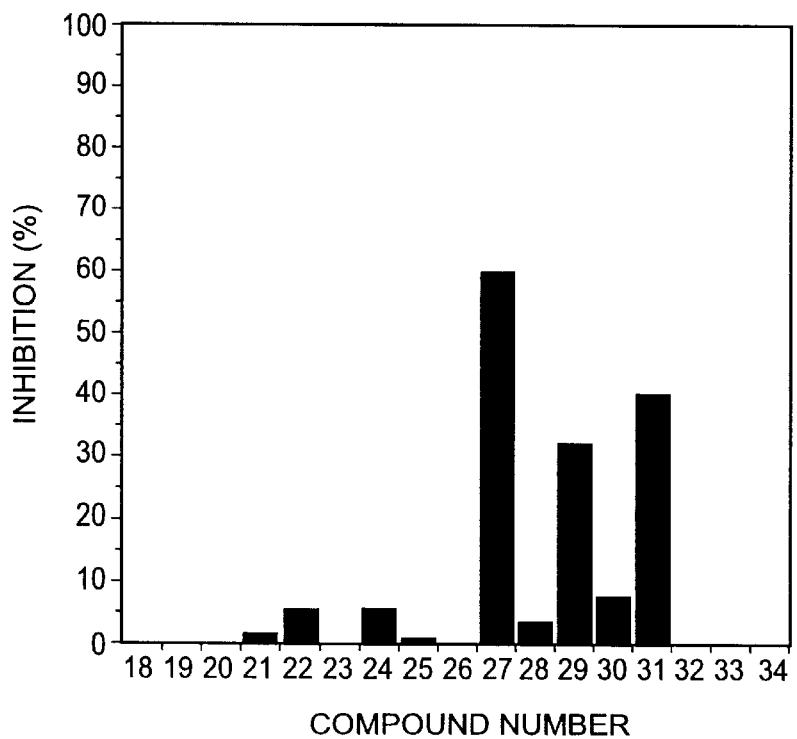

Measurements for each of the test compounds were performed twice, and the average inhibitory activity was determined. Results are shown in FIGS. 9A and 9B. Compound 27 (Ellagic acid), Compound 29 (Aclacinomycin A) and Compound 31 (heparin) exhibited potent inhibitory activity compared to any of the other test compounds.

TABLE 1

| No. | Compound |
|---|---|
| 1 | Samarosporin |
| 2 | Hydroxy aspergillic acid |
| 3 | Kidamycin |
| 4 | Siccanin |
| 5 | Comenic acid |
| 6 | Kinetin |
| 7 | 2-Chloro-4,6-bisethylamino-5-triazine |
| 8 | Methyl hesperidine |
| 9 | Oxyperitin |
| 10 | Protionamide |
| 11 | Quercetin |
| 12 | Flavone |
| 13 | Glycyrrhizin |
| 14 | Naringenin |
| 15 | 2-Hydroxychalcone |
| 16 | N-(Methylamino)-succinamide |
| 17 | D-(+)-Catechin |
| 18 | 2-Carbethoxy-5,7-dihydroxy-4-methoxyisoflavone |
| 19 | (−)-Epicatechin |
| 20 | Betulin |
| 21 | α-naphtoflavone |
| 22 | Curcumin |
| 23 | Tamarixetin-7-rutinoside |
| 24 | Aescin |
| 25 | Ursolsaure |
| 26 | Fisetin |
| 27 | Ellagic acid |
| 28 | Oleanolsaure |
| 29 | Aclacinomycin A |
| 30 | Sulfonazo III |
| 31 | Heparin |
| 32 | Chondroitin sulfate |
| 33 | Vitamin $B_{12}$ |
| 34 | Vitamin $B_6$ |

Example 12

Binding Assay for IGF and IGFBP-3 to ALS in a Solid Phase System (1)

In accordance with the conditions described in Example 10, streptavidin (1 µg/ml) was added to a microtiter plate in an amount of 50 µl/well and allowed to stand overnight at 4° C. for immobilization. After blocking with the blocking buffer, biotinylated RALS (rat ALS of Example 7: 50 ng/ml; Amersham International plc) was added in an amount of 50 µl/well, followed by incubation at 25° C. for 2 hours. RBP-3 E. coli (final concentration: 25 ng/ml) was added to the reaction mixture, and as a test compound, IGF-I or IGF-II in various concentrations were added simultaneously in a total amount of 50 µl/well. Plates were incubated overnight at 4° C. to form a ternary complex. The anti-RBP-3 pAb #35 (3

μg/ml) obtained in Example 8, was added in an amount of 50 μl/well to each of the wells containing the ternary complex, followed by incubation at 25° C. for 2 hours. A labeled secondary antibody (anti-rabbit IgG, horseradish peroxidase linked whole antibody, diluted to 1000-fold, product of Amersham International plc) was added in an amount of 50 μl/well, and the mixture was incubated at 25° C. for 2 hours. Finally, an ABTS solution was added in an amount of 100 μl/well and the mixture was allowed to stand at room temperature for 20 minutes. The absorbance (O.D.) at 405 nm. was then measured.

The value (absorbance) when IGF-I or IGF-II is added as a test compound is designated as "B", while the value (absorbance) when 300 pM of IGF-II is added as a test compound is designated as total bound (100%). The value (absorbance) when assayed without the addition of biotinated RALS is designated as nonspecific bound (NSB). The percent binding is calculated from the following equation:

(B−NSB)/(total bound−NSB)×100

Figure 10:
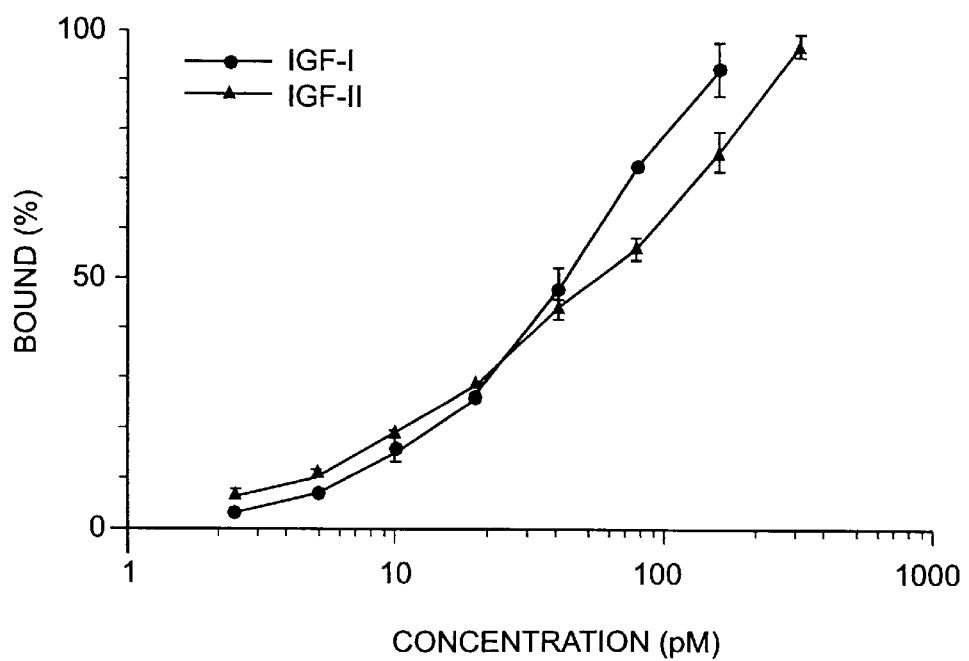
FIG. 10 illustrates the binding of IGFBP-3 to immobilized RALS in the presence of IGF-I or IGF-II, indicating the capacity of each of IGF-I and IGF-II to form the complex of IGF, IGFBP-3 and ALS.

The measurements for each condition were performed in triplicate. The average percent binding is plotted, and the SD is indicated by a bar (refer to FIG. 10).

The aforementioned binding assay allows one to evaluate the capacity of, for example, IGF or an IGF derivative to form a ternary complex with IGFBP and ALS. In addition, it is possible to screen for compounds that inhibit the formation of the ternary complex of IGF, IGFBP and ALS by adding the compound simultaneously (or before and after the addition) of RBP-3 *E. coli* and IGF-I or IGF-II.

Example 13

Binding Assay for IGF and IGFBP-3 to ALS in a Solid-Phase System (2)

In accordance with the conditions described in Example 10, streptavidin (1 μg/ml) was added to a microtiter plate in an amount of 50 μl /well and allowed to stand overnight at 4° C. for immobilization. After blocking with the blocking buffer, biotinated RALS (200 ng/ml) was added in an amount of 50 μl/well, followed by incubation at 250° C. for 2 hours. HRP-IGF-II (final concentration: diluted to 2000-fold) and RBP-3 *E. coli* (final concentration: 25 ng/ml) were added simultaneously in a total amount of 50 μl/well, and incubated at 25° C. for 2 hours. In the final step, after washing, an ABTS solution was added in an amount of 100 μl/well and the mixture was allowed to stand at room temperature for 20 minutes. The absorbance (O.D.) at 405 nm was then measured.

In an actual competitive binding assay, biotinylated RALS, HRP-IGF-II (final concentration: diluted to 1/2000), RBP-3 *E. coli* (final concentration: 25 ng/ml), and various concentrations of RALS, as a competitive inhibitor, were allowed to react.

The absorbance assayed without the addition of biotinated RALS is designated as nonspecific bound (NSB). The absorbance assayed without an inhibitory compound is designated as "$B_0$" and that assayed with the addition of an inhibitory compound is designated as "B". The percent binding of IGFBP-3 and IGF-II to immobilized RALS in the presence of the competitive inhibitor, RALS, is calculated from the following equation:

(B−NSB)/($B_0$−NSB)×100

Figure 11:
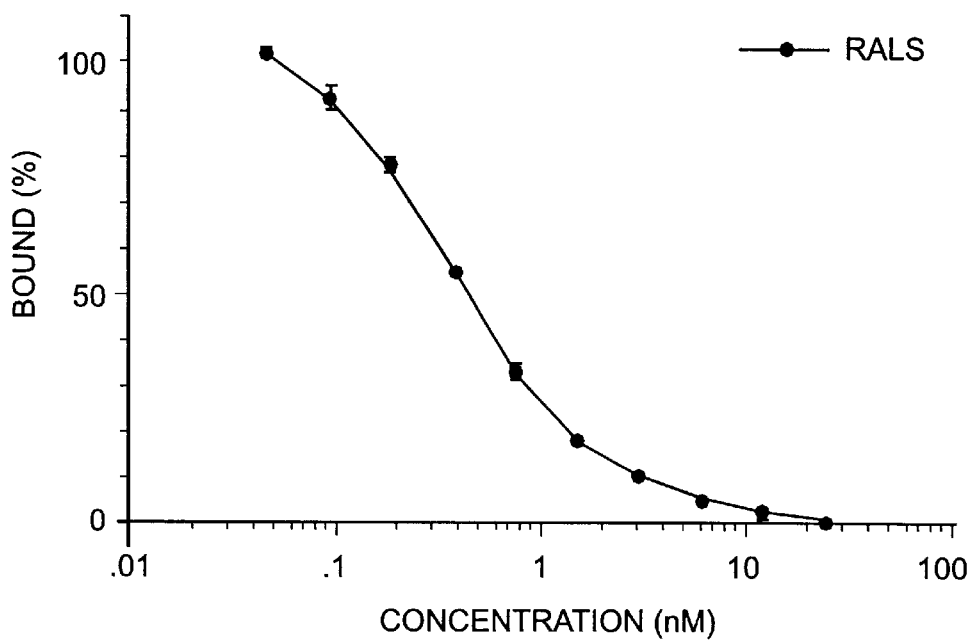
FIG. 11 illustrates the affinity of ALS for the complex of IGF and IGFBP-3 (Example 13).

The measurement for each concentration of RALS was performed in triplicate. The average percent value is plotted and the SD value is indicated by a bar (refer to FIG. 11).

The aforementioned binding assay allows one to evaluate the affinity of, for example, ALS or various ALS derivatives for the complex of IGF and IGFBP-3, in addition to screening for inhibitors of the ternary complex of IGF, IGFBP and ALS, or the binary complex of IGF and IGFBP-3 to ALS.

Example 14

Binding Assay for IGFBP-3 to ALS in a Solid Phase System

In accordance with the conditions described in Example 10, streptavidin (1 μg/ml) was added to a microtiter plate in an amount of 50 μl/well and allowed to stand overnight at 4° C. for immobilization. After blocking with a blocking buffer, biotinated RALS (200 ng/ml) was added in an amount of 50 μl/well, followed by incubation at 25° C. for 2 hours. RBP-3 *E. coli* (100 ng/ml) was added in an amount of 50 μl/well, and incubated overnight at 4° C. The anti-RBP-3 pAb #35 (3 μg/ml) obtained in Example 9, was added in an amount of 50 μl/well, followed by incubation at 25° C. for 2 hours. A secondary antibody was added in an amount of 50 μl/well, followed by incubation at 25° C. for 2 hours. In the final step, an ABTS solution was added in an amount of 100 μl/well, and the mixture was allowed to stand at room temperature for 20 minutes. The absorbance (O.D) at 405 nm was then measured.

In an actual a competition assay, biotinylated RALS, RBP-3 *E. coli* (final concentration: 100 ng/ml) and, various concentrations of RALS in a total amount of 50 μl/well, were allowed to react.

The absorbance value in the absence of biotinylated RALS is designated as nonspecific bound (NSB). The absorbance value in the absence of an inhibitor is designated as "$B_0$", and the absorbance value in the presence of an inhibitor is designated as "B". The percent binding of RBP-3 *E. coli* to immobilized RALS in the presence of the competitive inhibitor, RALS, is calculated from the following equation:

(B−NSB)/($B_0$−NSB)×100

Figure 12:
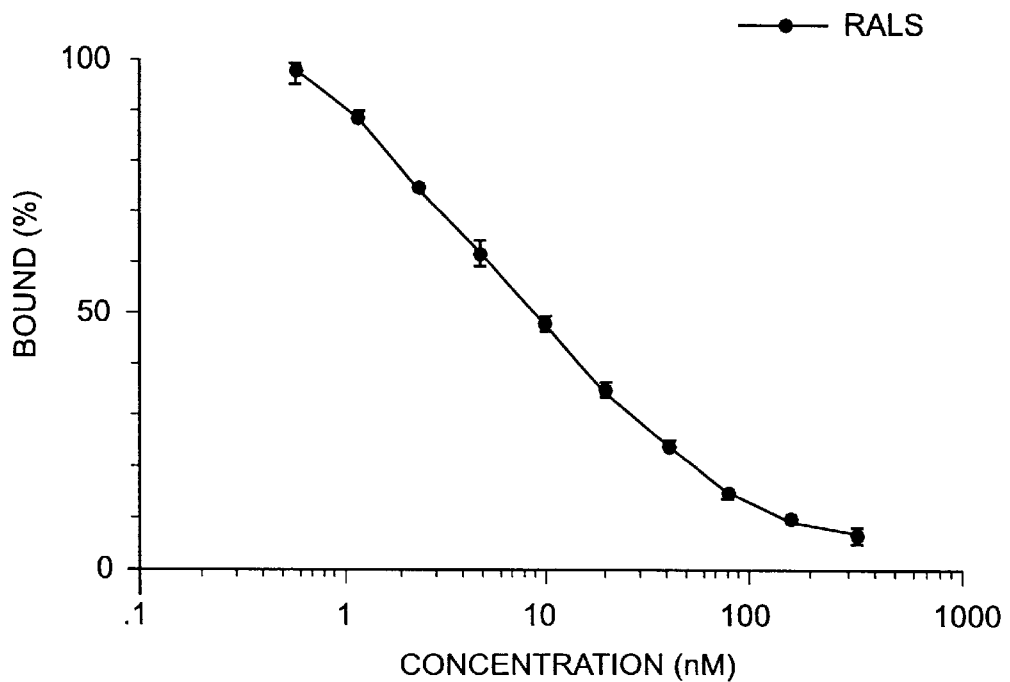
FIG. 12 illustrates the affinity of ALS for IGFBP-3 (Example 14).

The measurement for each concentration of inhibitor was performed in triplicate. The average absorbance is plotted and the SD value is indicated by a bar (refer to FIG. 12).

Based on the aforementioned binding assay, it is possible to evaluate the affinity of, for example, ALS or an ALS derivative for. IGFBP-3, in addition to screening for compounds, which inhibit the formation of the complex of IGFBP-3 and ALS.

Example 15

Characterization of Human IGF-II Derivative [Leu27, Leu43]rIGF-II, In Vitro (1)

The [Leu27, Leu43]rIGF-II derivative described in Example 8, was characterized for its binding affinity to human placental IGF-I receptor and human placental insulin receptor using a radioreceptor assay (Le Bon, T. R., et al., J. Biol. Chem., 261, 7685 (1986); Fujita-Yamaguchi, Y., et al., J. Biol. Chem., 258, 5045 (1983)).

In the first step, $^{125}$I-IGF (or $^{125}$I-insulin) (Amersham International plc) in an amount of 2×10$^4$ cpm was incubated with various amounts of the IGF receptor or the insulin receptor, to determine an amount of the receptor to which 50% of $^{125}$I-IGF (or $^{125}$I-insulin) binds.

[Leu27, Leu43]rIGF-II was added at various concentrations to aliquots of the mixture containing the determined amount of the receptor and $^{125}$I-IGF (or $^{125}$I-insulin) (2×10$^4$ cpm). The final volume of the reaction mix was brought to 300 μg using a 50 mM Tris-HCl buffer (pH 7.4) containing 0.1% BSA and 0.075% Triton X-100, and allowed to incubate overnight at 4° C. After incubation, 75 μg of human γ-globulin (4 mg/ml) and 375 μg of 20% PEG 6000 (pH 7.0) were added simultaneously, followed by incubation at 4° C. for 1 hour. The reaction mixture was centrifuged (3000 rpm×30 min, 4° C.), the supernatant decanted, and the cpm value for the pellet was measured by gamma counting.

In a control assay, the IGF-I receptor assay was performed using various concentrations of IGF-I or IGF-II instead of [Leu27, Leu43]rIGF-II. For the insulin receptor assay, various concentrations of insulin or IGF-II were added instead of [Leu27, Leu43]rIGF-II.

The cpm value in the absence of a receptor is designated as nonspecific bound (NSB). The cpm value in the absence of a test compound is designated as "B$_0$" and the cpm value assayed in the presence of a test compound is designated as "B". The percent binding to a receptor is calculated from the following equation:

(B−NSB)/(B$_0$−NSB)×100

The measurement for each concentration of test compound is performed in triplicate. The average cpm is plotted and the SD value is indicated by a bar.

Figure 13:
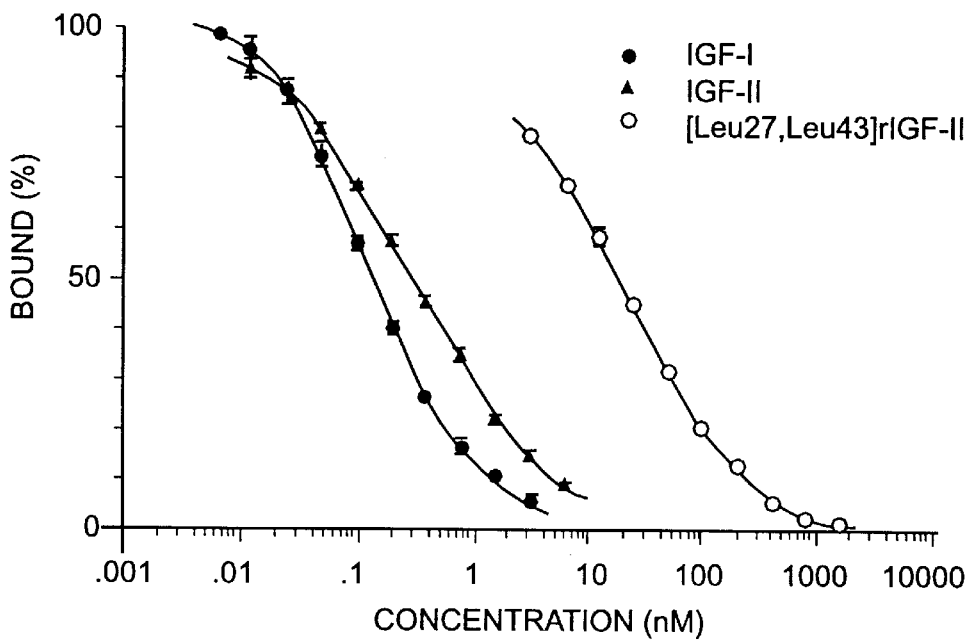
FIG. 13 illustrates the IGF-I receptor binding assay using $^{125}$I-IGF-I and the IGF-I receptor (Example 15).

FIG. 13 illustrates the results of the IGF-I receptor-binding assay using $^{125}$I-IGF-I and the IGF-I receptor. The affinity of IGF-II for an IGF-I receptor was similar to that of IGF-I, but the affinity of [Leu27, Leu43]rIGF-II for the IGF-I receptor decreased to about 1 to 2% of that for IGF-I.

Figure 14:
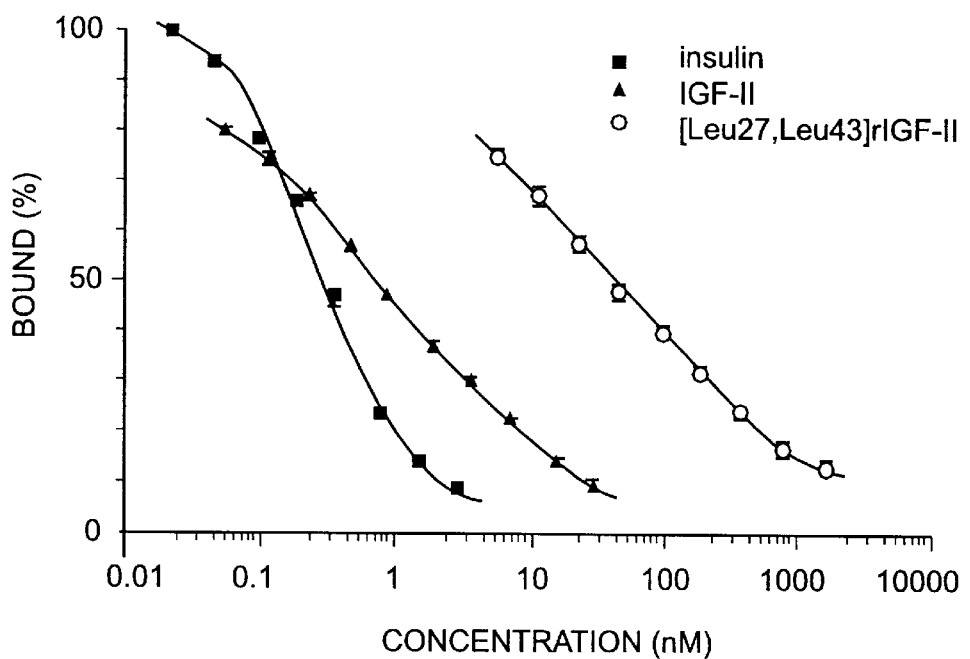
FIG. 14 illustrates the results of the insulin receptor binding assay using $^{125}$I-insulin and insulin receptor (Example 15).

FIG. 14 illustrates the results of the insulin receptor-binding assay using $^{125}$I-insulin and the insulin receptor. The affinity of IGF-II for an insulin receptor was similar to that of insulin, but the affinity of [Leu27, Leu43]rIGF-II for the insulin receptor decreased to about 1 to 2% of that for insulin.

Example 16

Characterization of Human IGF-II Derivative ([Leu27, Leu43]rIGF-II), In Vitro (2)

In accordance with the procedure of Example 10, the inventors determined that [Leu27, Leu43]rIGF-II inhibits the binding of IGF and IGFBP-3.

Figure 15:
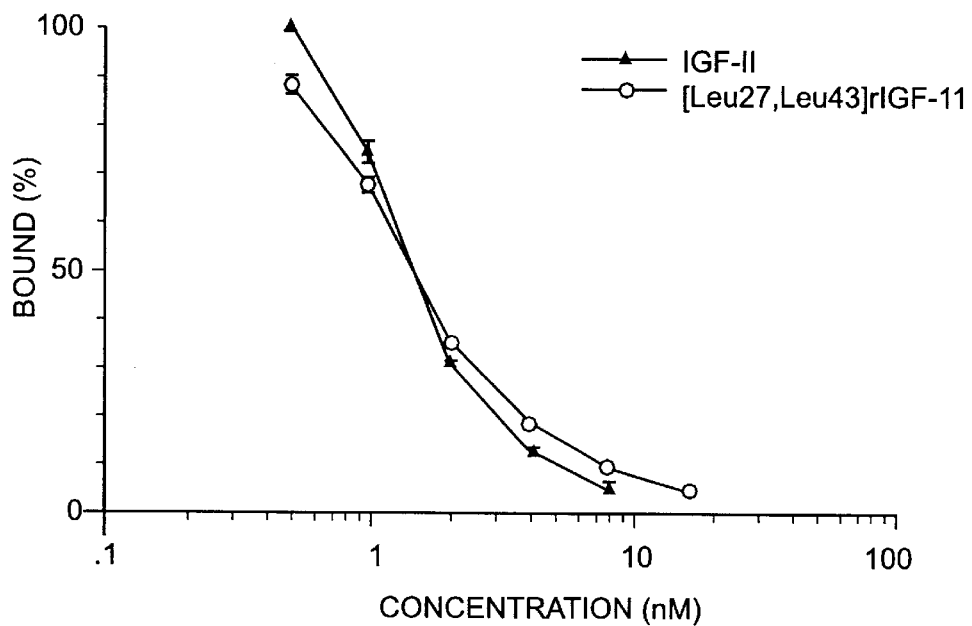
FIG. 15 illustrates the inhibition of the binding of IGF and IGFBP-3 by a human IGF-II derivative, [Leu27, Leu43] rIGF-II (Example 16).

[Leu27, Leu43]rIGF-II inhibited the binding of labeled IGF-II to immobilized IGFBP-3 at concentrations similar to those seen for IGF-II (refer to FIG. 15)

Example 17

Characterization of Anti-IGFBP-3 Antibody

Using the procedure of Example 10, the anti-IGFBP-3 antibodies (anti-RBP-3 pAb) of Example 9 were shown to inhibit the binding of IGF and IGFBP-3.

The antibodies, #35 and #90, exhibited the strongest inhibitory activity; 0.2632% as a molar ratio (2% as a weight ratio) when the activity of RBP-3 E. coli (IGFBP-3) was set at 100%. The antibodies, #36 and #89, exhibited almost the same inhibitory activity; 0.0875% as a molar ratio, while the antibody, #88, exhibited slightly less activity; 0.0525% as a molar ratio.

Figure 16:
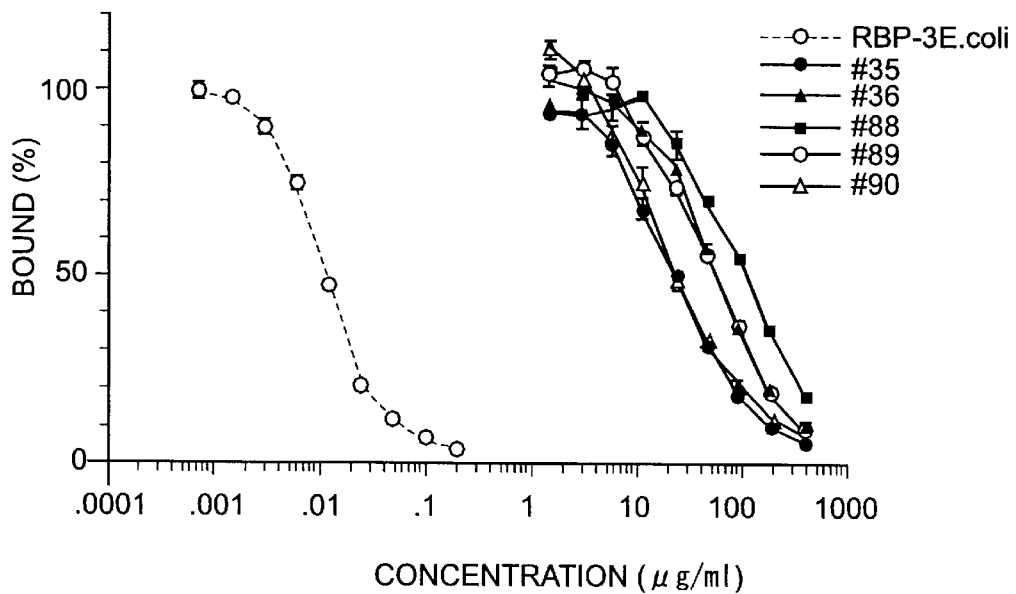
FIG. 16 illustrates the inhibition of the binding of IGF and IGFBP-3 by an anti-IGFBP-3 antibody (Example 17).

All of the inventive antibodies inhibited the binding of IGF and IGFBP-3 (refer to FIG. 16).

Example 18

Characterization of Human IGF-II Derivative and Anti-IGFBP-3 Antibody, In Vivo

To determine the effectiveness of the inventive method and the inventive compound, in vivo, the following experiments were conducted:

(1) the compound of the present invention was administered, in vivo, to compare its effects to IGF, and (2) the compound of the present invention was administered, in vivo, to determine if it increased the concentration of free IGF-I in the blood of a rat.

It is well known that administration of IGF, in vivo, results in the lowering of blood lipid levels. Its recognized specific effects are:

(a) lowering the level of free fatty acid (Turkalj. I., et al., J. Clin. Endocrinol. Metab., 75, 1186 (1992)), (b) lowering the level of triglyceride (Turkalj. I., et al., J. Clin. Endocrinol. Metab., 75, 1186 (1992); Zenobi, P. D., et al., J. Clin. Invest 90, 2234 (1992)), (c) lowering of total cholesterol vis-à-vis the lowering of LDL-cholesterol (Kazumi, T., Metabolism, 35, 1024 (1986); Zenobi, P. D., et al., Diabetologia 36, 465 (1993)), and the like.

The present inventors next investigated whether these same effects are brought about by the administration of the inhibitory compounds of Examples 8 and 9.

Example 18-1

Evaluation of Blood Lipid Level (1)

[Leu27, Leu43]rIGF-II (1,000 μg/kg) was administered, subcutaneously, to a group of nonfasting SD rats (n=3, 8 weeks old, male, average weight: 300 g, purchased from Charles River Japan).

Anti-RBP-3 pAb #35 (20 mg/head) was administered, intraperitoneally, to another group of SD rats.

As a negative control, physiological saline (500 μl/head) was administered, subcutaneously, and as a positive control group, IGF-I (50 μg/kg, 200 μg/kg) was administered, subcutaneously.

About 500 μl of blood was sequentially collected into EDTA-coated glass tubes from the caudal vein. Thirty minutes after collection, the blood was centrifuged (3,500 rpm×12 mm 25° C.), and plasma supernatant was recovered and stored at −80° C. until assayed. The total cholesterol and total triglyceride concentrations of the plasma were measured in accordance with a "Hitachi 715 model" automatic analyzer using the enzyme method of "Autocera CH02 and TG2" (each, manufactured by Daiichi Pure Chemicals Co., Ltd.).

Figure 17:
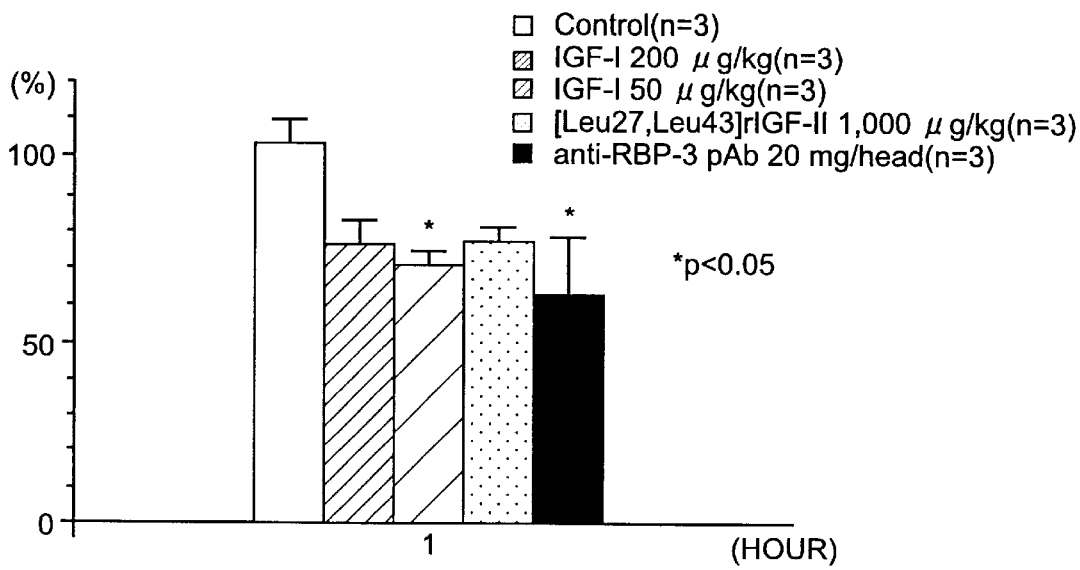
FIG. 17 illustrates the total triglyceride concentration in the blood of SD rats, 6 and 24 hours after the administration of IGF-I, IGF-II, IGF-II derivative and anti-IGFBP-3 antibody (Example 18-1).

Compared to the negative control group, the total glyceride concentration 6 hours after the administration of IGF-I (50 μg/kg) and anti-RBP-3 pAb #35 was significantly decreased, and [Leu27, Leu43]rIGF-II showed a tendency toward lowering total glyceride levels as well (refer to FIG. 17). Compared to the negative control group, the total cholesterol concentration 6 and 24 hours after the administration of IGF-I (200 μg/kg) was significantly decreased. A significant decrease 24 hours after the administration of (Leu27, Leu43]rIGF-II was also observed. The lowering tendency was also recognized even after the administration of anti-RBP-3 pAb #35 (refer to FIG. 18).

The administration of the inventive inhibitory compounds reduced lipid levels to that seen for IGF-I.

Figure 18:
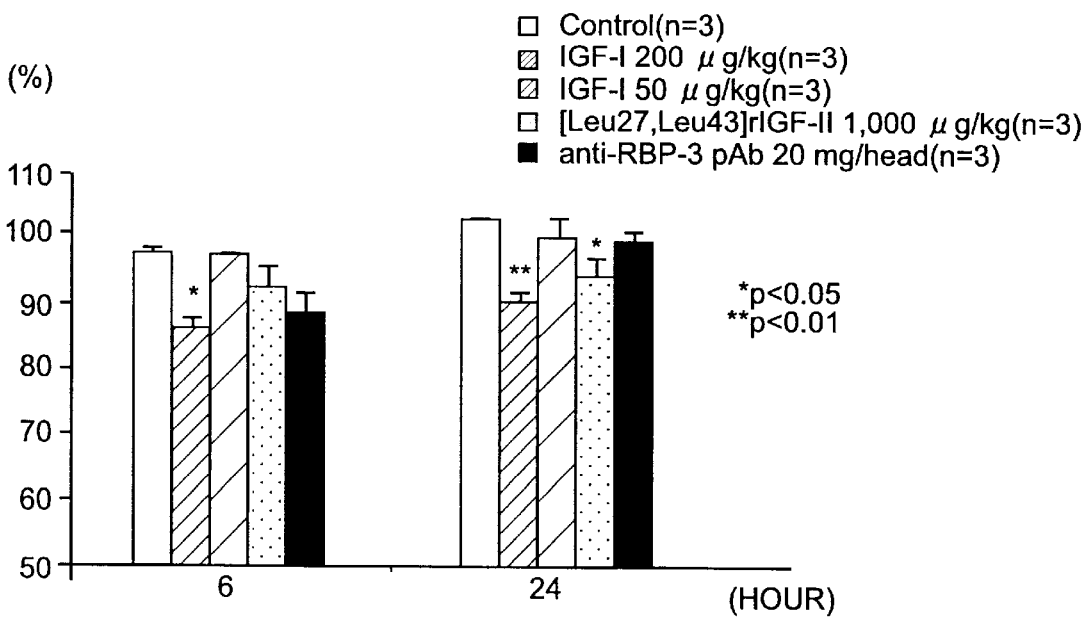
FIG. 18 illustrates the total cholesterol concentration in the blood of SD rats, 6 and 24 hours after the administration of IGF-I, IGF-II, IGF-II derivative and anti-IGFBP-3 antibody (Example 18-1).

FIGS. 17 and 18 demonstrate the results obtained from the inventive compounds: the percent concentrations of the total triglyceride and total cholesterol are shown before and after administration of the compounds.

Example 18-2

Evaluation of Blood Lipid Level (2)

Zucker fatty rats (insulin-resistant rat model, 6 to 11 weeks old, male, purchased from Tokyo Jikken Dobutsusha)

were fasted 20 hours before administration. The anti-RBP-3 pAb #36 (40 mg/head, n=5) was administered, subcutaneously, to a group of the fasting rats.

As a negative control group, physiological saline (500 µl/head, n=18) was administered, subcutaneously, and as a positive control, IGF-I (300 µg/kg, n=8) or IGF-II (1,200 µg/kg, n=8, or 600 µg/kg, n=B) was administered, subcutaneously. From each group, blood was collected 6 hours after administration. The total cholesterol and total triglyceride concentrations in the plasma were measured in accordance with Example 18-1. Based on the enzyme method of "NEFAC-test Wako" (product of Wako Pure Chemicals), the concentration of free fatty acid in plasma was measured in a 96-well microtiter plate (Costar) with a $\frac{1}{20}$ scale in the standard operating method, and then measuring the absorbance (Abs 550 nm) by a plate reader ("VMAX™", product of Molecular Devices Ltd.).

Figure 19:
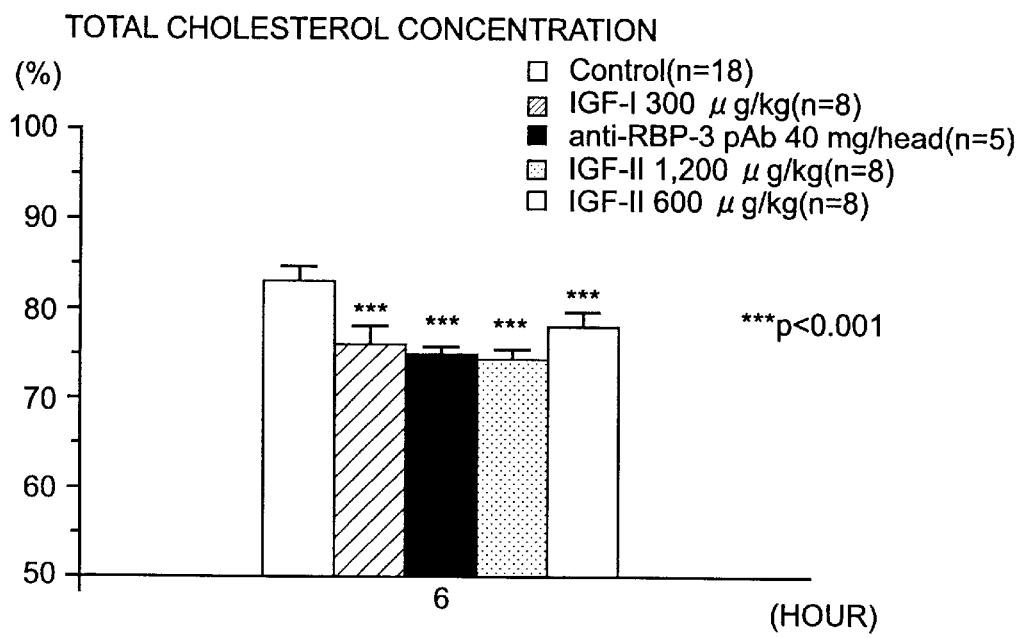
FIG. 19 illustrates the total cholesterol concentration in the blood of an insulin-resistant rat, 6 hours after the administration of IGF-I and anti-IGFBP-3 antibody (Example 18-2).

Compared to the negative control group, the total cholesterol concentration showed a significant decrease for all of the treatment groups 6 hours after administration (refer to FIG. 19). As regards the total glyceride concentration, a significant decrease was observed for all of the treatment groups 6 hours after administration (refer to FIG. 20). A similar decrease in concentration for free fatty acid was also observed for the treatment groups (refer to FIG. 21).

The administration of an inhibitory antibody (i.e., anti IGFBP-3 antibody which inhibits the binding of IGF and IGFBP-3) mediates the lowering of lipid levels such as that seen with IGF-I.

Figure 20:
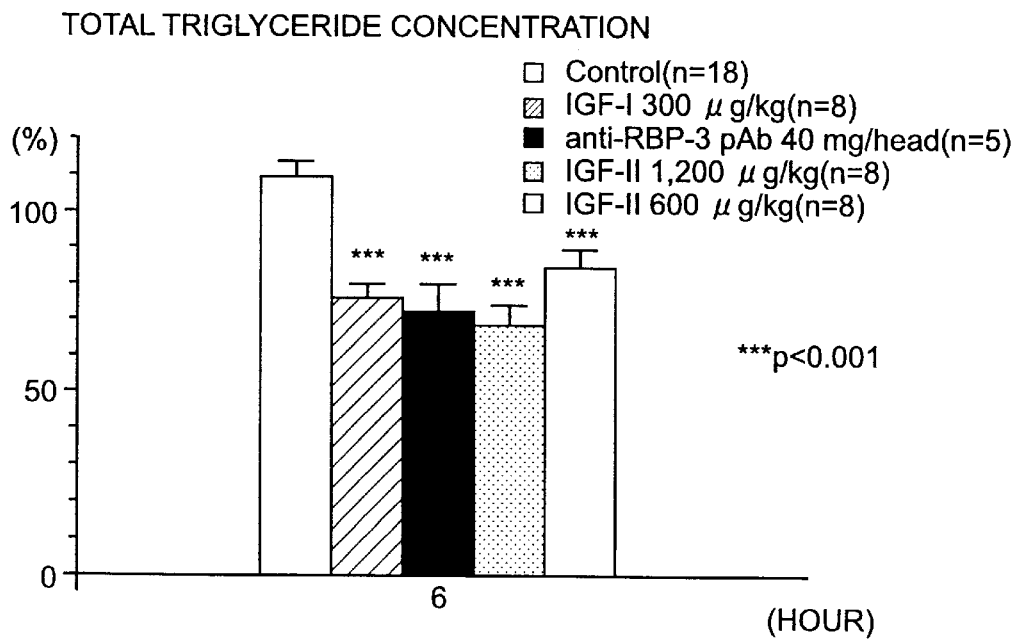
FIG. 20 illustrates the total triglyceride concentration in the blood of an insulin-resistant rat, 6 hours after the administration of IGF-I and anti-IGFBP-3 antibody (Example 18-2).
Figure 21:
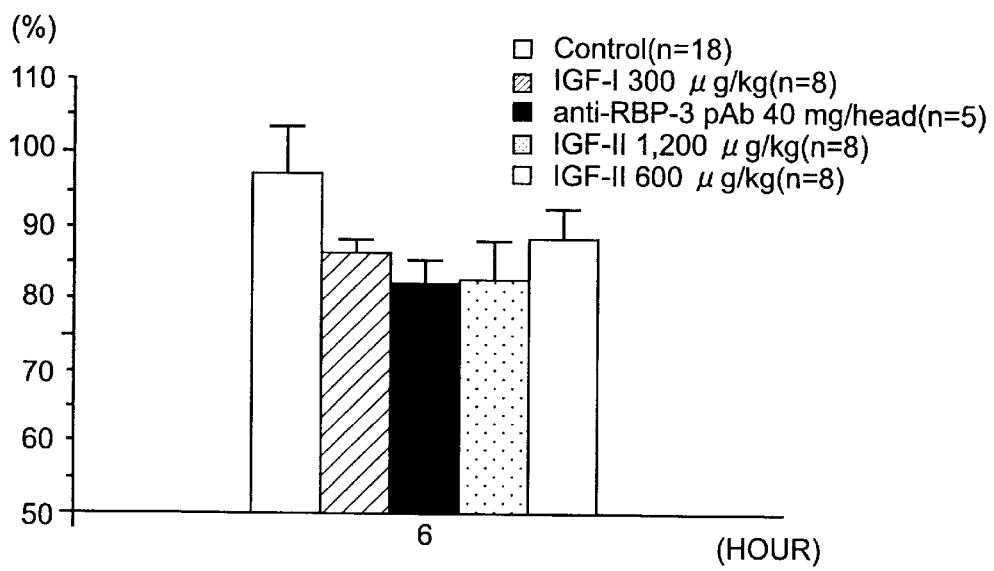
FIG. 21 illustrates the free fatty acid concentration in the blood of an insulin-resistant rat, 6 hours after the administration of IGF-I and anti-IGFBP-3 antibody (Example 18-2).

In FIGS. 19, 20 and 21, the percent concentrations for total cholesterol and total triglyceride are shown before and after administration of the inventive inhibitory compound.

Example 18-1

Evaluation of Free IGF-I Level in Blood

The anti-RBP-3 pAb #90 (40 mg/head) was administered, intraperitoneally, to a group of non-fasting SD rats (n=7, 8 weeks old, male, 10 average weight: 300 g, purchased from Charles River Japan). As a negative control group, physiological saline (500 µl/head) was administered, subcutaneously. The sequential blood collection was carried out in accordance with Example 18-1.

Free IGF-I levels in plasma and total IGF-I levels in plasma were analyzed by a reverse-phase cartridge ("Sep-Pak C18 cartridge") method (Hizuka, N., et al., Growth Regulation, 1, 51 (1991)) and the formic acid/acetone extraction method (Bowsher, R. R., et al., Endocrinology, 128, 805 (1991), respectively.

The rat IGF-I radioimmunoassay was carried out under conventional methods (Moses, A. C., et al., Eur. J. Biochem., 103, 401 (1980); Daughaday, W. H., Methods Enzymol., 146, 248 (1987)). $^{125}$I-IGF-I and somatomedin-C antiserum (anti IGF-I antibody), each produced by Eiken Chemical Ltd., were used and rat IGF-I produced by Gropep Pty Ltd. was used as standard. In the first step, $^{125}$I-IGF-I (7.77×103 cpm/100 µl), approximately 50 µg of antiserum, the IGF-I standard and test compound were mixed. The mixture was adjusted to 300 µl with an assay buffer (25 mM sodium phosphate buffer (pH 7.5) containing 0.25% BSA, 0.05% Tween 20 and 0.1% NaN$_3$) and incubated overnight at 4° C. To the mixture, 75 µl of 4 mg/ml human γ-globulin and 375 µg of 25% PEG 6000 were added, and the mixture incubated at 4° C. for 1 hour, followed by centrifugation (3,000 rpm×20 mm, 4° C.). The supernatant was decanted and the cpm incorporation in the pellet was measured by γ-counting.

Figure 22:
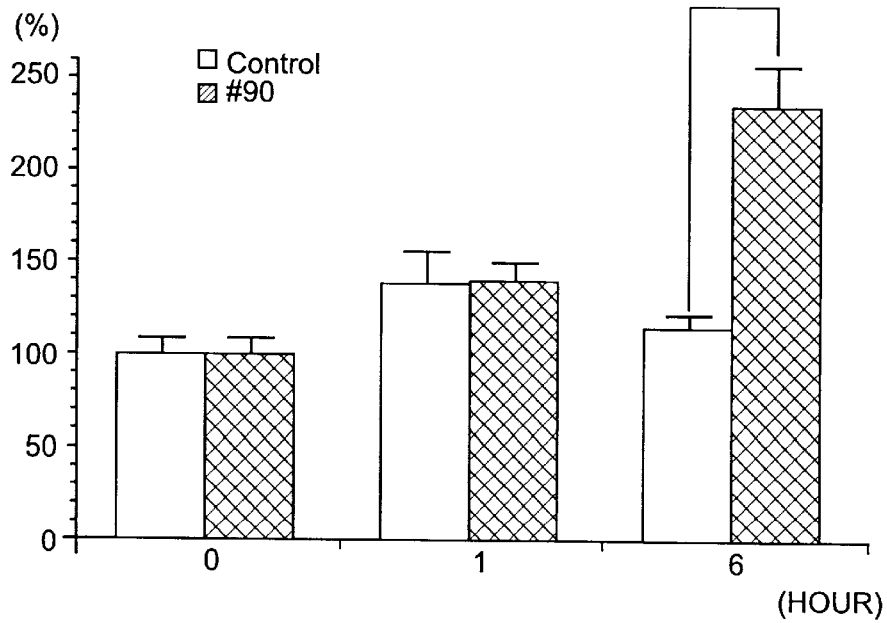
FIG. 22 illustrates the free IGF-I concentration in the blood of SD rats, i and 6 hours after the administration of anti-IGFBP-3 antibody (Example 18-3).

Compared to the negative control, the concentration or ratio of free IGF-I to total IGF-I showed a significant increase 6 hours after the administration of anti-RBP-3 pAb#90 (refer to FIG. 22).

In FIG. 22, the ratios of free IGF-I/total IGF-I) 1 and 6 hours after administration are shown.

---

What is claimed is:

1. An insulin-like growth factor (IGF) derivative, which binds to an IGF-binding protein 3, said derivative comprising an amino acid sequence of human insulin-like growth factor-II wherein a tyro sine residue at position 27 and a valine residue at position 43 in said human insulin-like growth factor-II are each substituted with a leucine residue, and wherein said derivative has reduced binding affinity for an IGF-I receptor or for an insulin receptor.

2. The insulin-like growth factor derivative of claim 1, wherein said derivative inhibits binding of an IGF-II and IGF-binding protein 3.

3. The insulin-like growth factor derivative of claim 1, wherein said derivative decreases total cholesterol and total triglyceride levels in blood upon administration of the said derivative.

4. A pharmaceutical composition comprising the insulin-like growth factor derivative of claim 1, and a pharmaceutically acceptable carrier.

5. A medicament, which comprises the insulin-like growth factor derivative as recited in claim 1.

6. A method for treating a disease which is responsive to IGF, said method comprising administering the derivative as recited in claim 1.

7. The method of claim 6, wherein the disease is at least one of diabetes, amyotrophic lateral sclerosis, or osteoporosis.

* * * * *